US006844192B2

(12) United States Patent
Orlando et al.

(10) Patent No.: US 6,844,192 B2
(45) Date of Patent: Jan. 18, 2005

(54) ADENOVIRUS E4 PROTEIN VARIANTS FOR VIRUS PRODUCTION

(75) Inventors: Joseph S. Orlando, Winston-Salem, NC (US); David A. Ornelles, Winston-Salem, NC (US)

(73) Assignee: Wake Forest University, Winston-Salem, NC (US)

(*) Notice: Subject to any disclaimer, the term of this patent is extended or adjusted under 35 U.S.C. 154(b) by 0 days.

(21) Appl. No.: 09/895,940

(22) Filed: Jun. 29, 2001

(65) Prior Publication Data

US 2003/0082811 A1 May 1, 2003

(51) Int. Cl.$^7$ .......................... C12N 5/10; C12N 15/63; C12N 15/861; C12N 15/864
(52) U.S. Cl. ................ 435/456; 435/235.1; 435/320.1; 435/69.1; 435/455; 435/457; 435/325; 435/366; 435/369; 536/23.1; 536/23.72
(58) Field of Search ............................. 435/456, 235.1, 435/320.1, 69.1, 455, 457, 325, 366, 369; 536/23.1, 23.72

(56) References Cited

U.S. PATENT DOCUMENTS

| | | |
|---|---|---|
| 5,604,090 A | 2/1997 | Alexander et al. |
| 5,658,776 A | 8/1997 | Flotte et al. |
| 5,693,531 A | 12/1997 | Chiorini et al. |
| 5,756,283 A | 5/1998 | Wilson et al. |
| 5,837,484 A | 11/1998 | Trempe et al. |
| 5,945,335 A | 8/1999 | Colosi |
| 6,001,650 A | 12/1999 | Colosi |
| 6,037,177 A | 3/2000 | Snyder |
| 6,040,183 A | 3/2000 | Ferrari et al. |
| 6,063,622 A | 5/2000 | Chamberlain et al. |

OTHER PUBLICATIONS

Boyer et al., J. Biol. Chem., May 19, 2000, vol. 275, No. 20, pp. 14969–14978.*

Orlando, Joseph S., et al., *An Arginine-Faced Amphipathic Alpha Helix is Required for Adenovirus Type 5 E4orf6 Protein Function*, Journal of Virology, vol. 73, No. 6, pp. 4600–4610 (Jun. 1999).

Amalfitano, Andrea, et al., *Production with Characterization of Improved Adenovirus Vectors with the E1, E2b, and E3 Genes Deleted*, Journal of Virology, vol. 72, No. 2, pp. 926–933 (Feb. 1998).

Allen, James M., et al., *Improved Adeno-Associated Virus Vector Production with Transfection of A Single Helper Adenovirus Gene, E4orf6*, Molecular Therapy, vol. 1, No. 1, pp. 88–95 (Jan. 2000).

Gao, Guang-Ping, et al., *A Cell Line for High-Yield Production of E1-Deleted Adenovirus Vectors Without the Emergence of Replication-Competent Virus*, Human Gene Therapy, vol. 11, pp. 213–219 (Jan. 1, 2000).

Bruder, Joseph T., et al., *Improved Production of Adenovirus Vectors Expressing Apoptotic Transgenes*, Human Gene Therapy, vol. 11, pp. 1393–149 (Jan. 1, 2000).

Weigerl, Silke, et al., *The Nuclear Export Signal within the E4orf6 Protein of Adenovirus Type 5 Supports Virus Replication and Cytoplasmic Accumulation of Viral mRNA*, Journal of Virology, vol. 74, No. 2, pp. 764–772 (Jan. 2000).

Sandig, Volker, et al., *Optimization of the helper-dependent adenovirus system for production and potency in vivo*, PNAS, vol. 97, No. 3, pp. 1002–1007.

* cited by examiner

Primary Examiner—David Guzo
(74) Attorney, Agent, or Firm—Myers Bigel Sibley & Sajovec

(57) ABSTRACT

A method of packaging a recombinant viral vector is carried out by: (a) providing a packaging cell, the packaging cell containing and expressing a nucleic acid encoding a mutant adenovirus E4orf6 protein, the E4orf6 protein containing at least one mutation that renders the protein non-toxic to the host cell; (b) transfecting or infecting the packaging cell with a nucleic acid that encodes a recombinant viral vector (e.g., an adenovirus vector or an adeno-associated virus vector), where the vector lacks a functional gene encoding E4orf6 protein; (c) culturing the transfected cells; and then (d) collecting packaged recombinant viral vector from the cultured cells. Nucleic acids, vectors and packaging cells used for carrying out the methods, as well as proteins utilized in the methods, are also described.

24 Claims, 12 Drawing Sheets

Figure 8

|  | 240 241 | 243 244 | 248 | 251 |
|---|---|---|---|---|
| Human Ad2/5 | A R R T R R L M L R A V R I I A E |
| Human Ad9  | A R R T R R L M L K A V G I I A R |
| Human Ad17 | A R R T R R L M L R A V G I I A R |
| Human Ad12 | A R R T R L L M L K V V Q V I A E |
| Human Ad40 | A R R T R R L L A K A V K V L G S |
| Porcine Ad3 | A Q R L R H W L K L A A E A I G A |
| Bovine Ad3 | L K R C K Q K I R Y M L N L A P K |
| Canine Ad1 | A F W V K S I I D R V L R E V - E |

ADENOVIRUS E4 PROTEIN VARIANTS FOR VIRUS PRODUCTION

STATEMENT OF FEDERAL SUPPORT

This invention was made with government support under grant number AI35589 from the National Institute of Health. The United States government has certain rights to this invention.

FIELD OF THE INVENTION

The present invention concerns packaging cells and methods of use thereof for the manufacture of viral vectors, particularly adenovirus and adeno-associated virus (AAV) vectors.

BACKGROUND OF THE INVENTION

One of the most promising methodologies in gene delivery is the use of adenovirus and adeno-associated virus as a viral vector. One of the major challenges in using adenovirus to deliver DNA to cells is that it is very difficult to create viruses carrying the DNA that also lack the viral E4 region. Adenovirus vectors that lack the E4 region are desirable because they can accept larger inserts of DNA and because they cannot express a toxic and mutagenic protein, the E4orf6 protein. It is difficult to create these viruses and to produce sufficient amounts of these viruses because the viral E4orf6 protein is needed for replication, but is cytotoxic to the cells in which the virus is replicated when supplied in trans. This cytopathic effect of the E4orf6 protein has been a severe roadblock to the development of successful nucleic acid delivery systems that use adenovirus and/or AAV.

Open reading frame 6 of the early region 4 (E4orf6) of group C adenovirus (Ad) encodes a multifunctional protein that enhances viral replication (reviewed in Leppard (1997) *J. Gen. Virol.* 78:2131–2138) and acts as an oncoprotein (Nevels et al. (1997) *Proc. Natl. Acad. Sci. USA* 94:1206–1211). Ad mutants that lack the entire E4 region are severely defective for viral DNA replication and late viral protein synthesis (Bridge and Ketner (1990) *Virology* 174:345–353; Halbert et al. (1999) *J. Virol.* 56:250–257; Huang and Hearing (1989) *J. Virol.* 63:2605–2615; Weiden and Ginsberg (1994)*Proc. Natl. Acad. Sci. USA* 91:153–157). However, expression of the E4orf6 protein in trans largely corrects the growth defect of an E4-deletion virus (Armentano et al. (1995) *Hum. Gene Ther.* 6:1343–1353; Halbert et al. (1985) *J. Virol.* 56:250–257; Ketner et al. (1989) *Nucleic Acids Res.* 17:3037–3048).

The E4orf6 protein increases late viral protein production by facilitating the cytoplasmic accumulation of mRNA at a postranscriptional level (Leppard (1997) *J. Gen. Virol.* 78:2131–2138; Nordqvist et al. (1994) *Mol. Cell Biol.* 14:437–445; Pilder et al. (1986) *Mol. Cell Biol.* 6:470–476). In addition to enhancing the processing and stability of late viral RNA in the nucleus (Dix and Leppard (1993) *J. Virol.* 67:3226–3231; Ohman et al. (1993) *Virology* 194:50–58), the E4orf6 protein, as part of a complex with the E1B-55 kDa protein, promotes the nucleocytoplasmic transport of processed late viral mRNA (Pilder et al. (1986) *Mol. Cell Biol.* 6:470–476; Rubenwolf et al. (1997) *J. Virol.* 71:1115–1123; Sarnow et al. (1984) *J. Virol.* 49:692–700). Additionally, the E4orf6-E1B-55 kDa protein complex blocks the nucleocytoplasmic transport of most host mRNAs (Babiss et al. (1985) *Mol. Cell Biol.* 5:2552–2558; Pilder et al. (1986) *Mol. Cell Biol.* 6:470–476).

It has been proposed that the E4orf6-E1B-55 kDa protein complex binds a key component of the host cell nucleocytoplasmic transport system to achieve the selective transport of late viral mRNA (Ornelles and Shenk (1991) *J. Virol.* 65:424–429). The E4orf6 protein also interferes with the host cell cycle, and in cooperation with the E1proteins of Ad, promotes oncogenesis of baby rat kidney (BRK) cells (Nevels et al. (1997) *Proc. Natl. Acad. Sci. USA* 94:1206–1211; Nevels et al. (1999) *Oncogene* 18:9–17). The E4orf6-mediated transformation of BRK cells may stem from the ability to bind and inactivate tumor suppressor proteins such as p53 or p73 (Dobner et al. (1996) *Science* 272:1470–1473; Higashino et al. (1998) *Proc. Natl. Acad. Sci USA* 95:15683–15687; Steegenga et al. (1999) *Mol. Cell Biol.* 19:3885–3894), to bind and inactivate the cyclin A protein (Grifman et al. (1999)*J. Virol.* 73:10010–10019), or to increase the host cell mutation rate (Moore et al. (1996) *Proc. Natl. Acad. Sci. USA* 93:11295–11301).

Some of the critical features of the E4orf6 protein required for its function have been identified. A protein fragment containing the amino-terminal 58 amino acids of the E4orf6 protein binds both the E1B-55 kDa protein and the tumor suppressor p53 protein in vitro (Dobner et al. (1996) *Science* 272:1470–1473; Rubenwolf et al. (1997) *J. Virol.* 71:1115–1123). Although the E4orf6/7 protein contains this sequence of amino acids and binds the E1B-55 kDa and p53 proteins in vitro, it cannot establish a functional interaction with the E1B-55 kDa protein in the cell (Orlando and Ornelles (1999) *J. Virol.* 73:4600–4610), elicit p53 degradation (Querido et al. (1997) *J. Virol.* 71:788–798), or induce transformation of BRK cells (Nevels et al. (1997) *Proc. Natl. Acad. Sci. USA* 94:1206–1211).

It has been reported that the E4orf6 protein contains a cryptic leucine-rich nuclear export signal (NES), centered around isoleucine-90 and leucine-92 (Dobbelstein et al. (1997) *EMBO J.* 16:4276–4284) that protein is necessary for E4orf6-mediated degradation of p53 (Nevels et al. (2000) *J. Virol.* 74:5168–5181). Although E4orf6 proteins lacking the amino terminus or the NES can cooperate with the E1B and E1A proteins to transform BRK cells, these cells are not as tumorogenic in nude mice cells as BRK cells transformed with the wild-type E4orf6 protein (Nevels et al. (2000) *J. Virol.* 74:5168–5181).

Several cysteine and histidine residues that are conserved between E4orf6 proteins from several Ad subgroups are essential for many functions of the E4orf6 protein. E4orf6 variants with substitutions among these amino acids fail to promote late viral gene expression, no longer co-immunoprecipitate with the E1B-55 kDa protein, fail to direct nuclear localization of the E1B-55 kDa protein, fail to promote destabilization of the p53 protein, transform BRK cells with reduced efficiency, and produce transformed cells with diminished oncogenic potential in nude mice (Boyer and Ketner (2000)*J. Biol. Chem.* 275:14969–14978; Nevels et al. (2000)*J. Virol.* 74:5168–5181). Boyer and Ketner have suggested that these conserved cysteine and histidine residues coordinate with two or more zinc ions to establish the proper tertiary structure of the E4orf6 protein (Boyer and Ketner (2000) *J. Biol. Chem.* 275:14969–14978).

The arginine-faced amphipathic α helix at the carboxy terminus of the E4orf6 protein is required for many of the functions of the E4orf6 protein. E4orf6 variants that lack this structure or contain proline substitutions within the α helix fail to promote virus replication (Orlando and Ornelles (1999) *J. Virol.* 73:4600–4610). Additionally, these E4orf6 variants fail to relocalize the E1B-55 kDa protein to the nucleus of cotransfected cells. The integrity of the arginine-faced amphipathic α helix is also required for E4orf6mediated p53 degradation (Nevels et al. (2000) *J.*

Virol. 74:5168–5181). Furthermore, it has been suggested that destabilization of p53 by the E4orf6 protein depends on binding both the E1B-55 kDa protein as well as uncharacterized cellular factors (Querido et al. (2001) *J. Virol.* 75:699–709). An intact arginine-faced amphipathic α helix is also required for the full oncogenic potential of the E4orf6 protein as measured by the ability to transform BRK cells and elicit an abnormal state of growth termed hypertransformation (Nevels et al. (2000) *J. Virol.* 74:5168–5181). Although these oncogenic functions may depend in part, on the E1B-55 kDa protein, it is possible that the arginine-faced amphipathic α helix of the E4orf6 protein interacts with some cellular factors that control cell growth. For example, a motif within the amphipathic α helix was suggested to bind cyclin A and augment expression of a transgene present on a recombinant adeno-associated virus (rAAV) (Grifman et al. (1999) *J. Virol.* 73:10010–10019). Since the E4orf6 effect on rAAV transgene expression resembled that seen upon treatment of rAAV-infected cells with inhibitors of DNA synthesis or DNA damaging agents, it is possible that the E4orf6 protein can perturb either the integrity of cellular DNA or the signaling pathways associated with DNA damage (Alexander et al. (1994) *J. Virol.* 68:8282–8287; Ferrari et al. (1996) *Science* 272:1470–1473; Jansen-Durr (1996) *Trends Genet.* 12:270–275).

As indicated above, it would be extremely useful to provide a way to supply the necessary functions of the E4orf6 protein in a helper cell for the production of viral vectors, while also reducing the cytotoxic effects of this protein.

SUMMARY OF THE INVENTION

Accordingly, a first aspect of the present invention is a method of packaging a recombinant viral vector. The method comprises comprising the steps of:

(a) providing a packaging cell, the packaging cell containing and expressing a nucleic acid encoding a mutant adenovirus E4orf6 protein, said E4orf6 protein containing at least one mutation that renders the protein non-toxic to the host cell;

(b) transfecting or infecting the packaging cell with a nucleic acid that encodes a recombinant viral vector (e.g., a vector selected from the group consisting of adenovirus vectors and adeno-associated virus vectors), where the vector lacks a functional gene encoding E4orf6 protein;

(c) culturing the transfected cells, preferably under conditions that permit expression of the mutant E4orf6 protein and the production of packaged recombinant viral vector therein; and then (d) collecting packaged recombinant viral vector from the cultured cells (which collecting step may be carried out at the same location or a different location from where the cells are cultured).

A second aspect of the present invention is a packaging cell useful in a method as described above. In general, the packaging cell contains and expresses a nucleic acid encoding a mutant adenovirus E4orf6 protein, the E4orf6 protein containing at least one mutation that renders the protein non-toxic to the packaging cell. Thus the mutant adenovirus E4orf6 protein is sufficient or effective for packaging or encapsidation of a virus in conjunction with other constituents or components necessary for packaging thereof.

A third aspect of the present invention is a nucleic acid (e.g., an isolated and/or purified nucleic acid) encoding a mutant adenovirus E4orf6 protein as described above. The nucleic acid may be provided in isolated form or in any suitable type of vector, including but not limited to plasmids, bacteriophages, cosmids, retroviruses and other viral and nonviral vectors.

A fourth aspect of the present invention is a mutant adenovirus E4orf6 protein as described above (e.g., an isolated and/or purified protein).

The foregoing and other objects and aspects of the present invention are explained in detail in the drawings herein and the specification set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows the key features of the amphipathic a helix are conserved among different serotypes of adenovirus. The predicted amino acid sequence of five human adenovirus E4orf6 proteins (Ad2/5. SEQ ID NO: 26: Ad9. SEQ ID NO: 28: Ad17. SEQ ID NO: 29: Ad12. SEQ ID NO: 30 and Ad4O. SEQ ID NO: 31) and three non-human adenovirus E4orf5 proteins (Porcine Ad3. SEQ ID NO: 32: Bovine Ad3. SEQ ID NO: 33 and Canine Ad1, SEQ ID NO: 34) that are similar to the human Ad E4orf6 protein were aligned at the region corresponding to aniphipathic α helix. The arginine residues found in the Ad2/5 protein are identified at the top of the alignment. Arginines that occur at the same position in the other proteins are shaded by black, basic amino acids in these positions are shaded gray and divergent amino acids are not shaded.

[cytoxicity] cytotoxicity is cell type-specific. The cells indicated on each panel were transfected with the indicated plasmids to express only the neomycin-resistance gene (vector) or the resistance gene and the non-functional praline-mutant ($L_{245}P$) or the wild-type E4orf6 protein (E4orf6). Two days after transfection, the cells were harvested and replated in triplicate at low cell density in the presence of 600 µg/ml G41 8. After 21 days, the number of neomycin-resistant colonies were counted and the values±SD plotted. Neomycin-resistant cell colonies could not be recovered from 293 cells transfected with the vector expressing the wild-type E4orf6 protein. This value is plotted as □1 in panel B.

Figure 11:
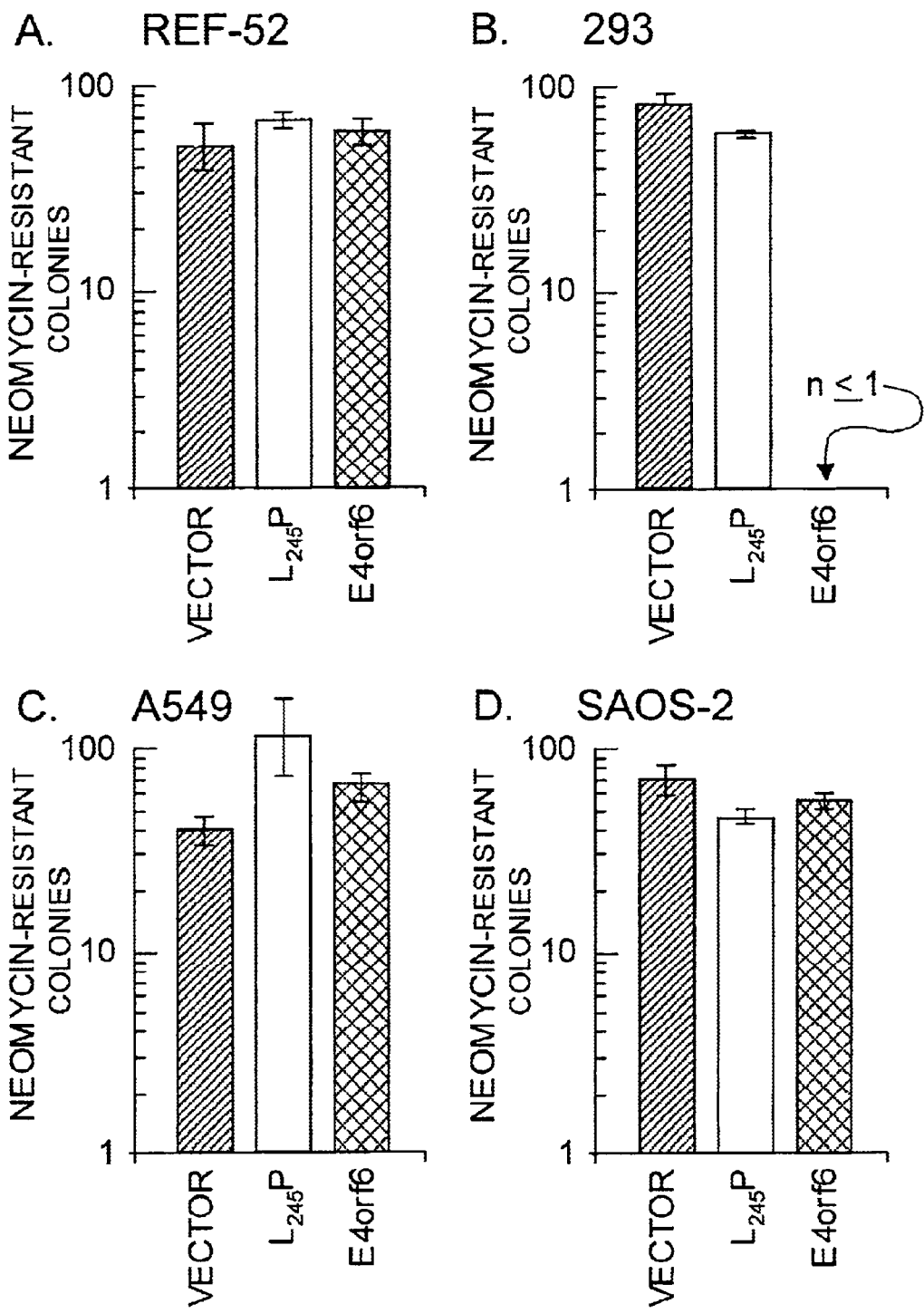
FIG. 11 (Parts A–D) shows that the inability to form neomycin-resistant cell colonies reveals that E4orf6
Figure 12:
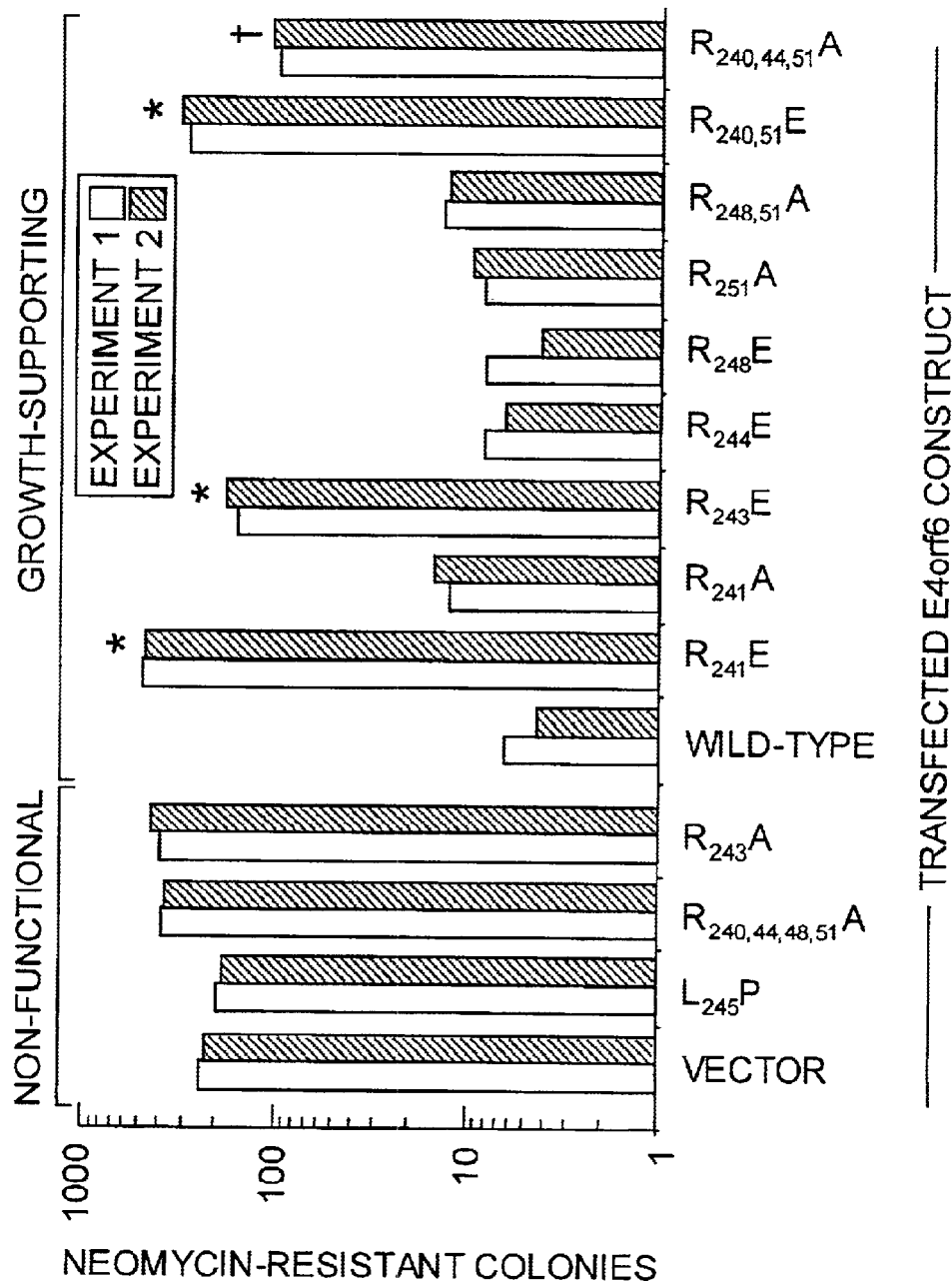

FIG. 12 shows that select E4orf6 substitution variants support the growth of an E4-deletion virus and are not cytotoxic. 293 cells were transfected with plasmids expressing the neomycin resistance gene (vector) or the neomycin resistance gene and the E4orf6 variant indicated. The transfected cells were selected for resistance to G418 as described in the legend to FIG. 11. Colonies of neomycin-resistant cells were counted 21 days after transfected. Representative results from two independent experiments are shown. Constructs that failed to complement growth of the E4-deletion virus are shown by the light bars. Constructs that provided E4orf6 function are shown by the dark bars. The (*) identifies E4orf6 variants that provided wild-type E4orf6 function during virus growth and were no more cytotoxic to 293 or HeLa cells than the vector or $L_{245}P$ control. The $R_{240,44,51}A$ variant (†) provided wild-type E4orf6 function during virus growth but was significantly more cytotoxic than the vector or $L_{245}P$ control.

DETAILED DESCRIPTION OF PREFERRED EMBODIMENTS

Except as otherwise indicated, standard methods may be used for the production of cloned genes, vectors, and transformed cells according to the present invention. Such techniques are known to those skilled in the art (see e.g., SAMBROOK et al., EDS., MOLECULAR CLONING: A LABORATORY MANUAL 2d ed. (Cold Spring Harbor, N.Y. 1989); F. M. AUSUBEL et al, EDS., CURRENT PROTOCOLS IN MOLECULAR BIOLOGY (Green Publishing Associates, Inc. and John Wiley & Sons, Inc., New York Nucleotide sequences are presented herein by single strand only, in the 5' to 3' direction, from left to right. Nucleotides are represented herein in the manner recommended by the IUPAC-IUB Biochemical Nomenclature Commission in accordance with 37 CFR §1.822 and established usage. See, e.g., Patent-In 3.0 User Manual, APPENDIX D page 2–3 (June 2000) (U.S. Patent and Trademark Office).

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"E4orf6 protein" as used herein refers to the protein produced by the adenovirus E4 region that embodies all of the functions of this region necessary for viral replication (i.e., deletion of other proteins encoded by the E4 region with retention of this region results in virus that can replicate at near-wild type levels). E4orf6 protein is generally encoded in open reading frame 6 (e.g., in group C adenoviruses or in human adenoviruses) but the homologous protein may be found to be expressed from other reading frames of the E4 region in other adenoviruses (e.g., E4orf5 in non-human adenoviruses). Numbering of amino acids of the E4orf6 protein may be carried out by alignment amino acids to the amino acid sequence of the human Ad2/5 virus E4orf6 protein amphipathic alpha helix region as shown in FIG. 8.

"Deleted" as used herein refers to the removal of a segment of a nucleic acid or protein, in whole or in part, so long as a sufficient portion to render the region functionally inactive is removed.

The applicants specifically intend that the disclosures of all United States patent references cited herein be incorporated herein by reference in their entirety.

1. Adenovirus and AAV Vectors.

Adenovirus vector as used herein refers to a vector derived from an Adenoviridae family, including those of both the Mastadenovirus and the Aviadenovirus genus, and including but not limited to avian, human, simian, bovine, equine, porcine, ovine, canine, and opossum viruses. Examples include but are not limited to *mastadenovirus H* subgroups A, B, C, D, E, and F. The vectors preferably have regions deleted to permit the incorporation of heterologous nucleic acid segments therein, and in a preferred embodiment have the region encoding the E4orf6 protein deleted.

Cell lines of the present invention may also be used for the production of Adeno-associated virus vectors. Adeno-associated (or "AAV") virus vector as used herein refers to a vector derived from an adeno-associated virus serotype, including without limitation Aav-1, Aav-2, Aav-3, Aav-4, AAV-5, AAVX7, etc. AAV vectors can have one or more of the AAV wild-type genes deleted in whole or part, preferably the rep and/or cap genes, but may retain functional flanking ITR sequences as necessary for the rescue, replication and packaging of the AAV virion. The ITRs need not be the wild-type nucleotide sequences and may be altered, e.g., by the insertion, deletion or substitution of nucleotides, so long as the sequences provide for functional rescue, replication and packaging.

2. E4orf6 Mutations.

A mutant adenovirus E4orf6 protein used to carry out the present invention is one which contains at least one mutation (e.g., a substitution or deletion mutation, preferably a substitution mutation) that renders the protein non-toxic to a host cell in which the protein is expressed, yet which protein retains the capability to produce encapsidated or packaged recombinant virus or viral vector in a transfected host cell. Thus the present invention is based on the discovery that mutations can be introduced into E4orf6 which render that protein non-toxic to host cells, yet do not disrupt the activity of the protein in viral packaging or encpasidation. In general, the mutations are in the amphipathic alpha helix region of E4orf6 protein, and disrupt or reduce the positive charge on the exposed surface domain of the amphipathic alpha helix sufficiently to render the protein non-toxic to the host cell (for the purpose of producing encapsidated or packaged virus) yet retains sufficient function of the wild-type protein to carry out packaging of virus or viral vector.

In some illustrative embodiments, the E4orf6 protein contains at least one mutation (e.g., one, two, three or more mutations) in the region containing amino acids 230 or 239 to 254 or 260 (e.g., in the region containing amino acids 239 to 254) that renders the protein non-toxic to a host cell (particularly mammalian host cells) in which the protein is expressed. In addition, the mutation may be a mutation that disrupts the interaction of the E4orf6 protein with the E1B-55 kDa protein in a host cell (that is, the activity of the protein to cause E1B-55 kDa to change cell location or translocate to the cell nucleus).

In general, mutations used to implement the present invention are substitution mutations in the amphipathic alpha helix region of the E4orf6 protein. Such substitution mutations may, for example, comprise a substitution mutation at one or more of positions 240, 241, 243, 244, 248, and/or 251. In general, such a substitution is a substitution of arginine for another amino acid that is compatible with the integrity of the alpha helix. Such amino acids include all of the amino acids except proline and glycine. For example, such a substitution may be a substitution of arginine for another amino acid that is hydrophilic or charged, but is not a basic amino acid, such as glutamic acid, aspartic acid, serine, threonine, cysteine, tyrosine, asparagine, and/or glutamine. By "non-toxic" to the host cell is herein meant that the protein is sufficiently non-toxic to enable a host cell to carry out its intended function of packaging a recombinant virus that does not itself encode E4orf6, when sufficient E4orf6 is expressed to carry out this function. Note that multiple mutations can be introduced if desired, whether or not such mutations provide a cumulative or synergistic benefit in non-toxicity, to reduce the probability of reversion to the wild-type sequence. Nucleic acids encoding such mutant proteins, along with constructs that contain and express such mutant proteins under the control of a heterologous promoter, may be produced in accordance with known techniques.

3. Packaging Cells and Use Thereof.

As noted above, the present invention provides a method of packaging (that is, encapsidating) a recombinant viral vector comprising the steps of: (a) providing a packaging cell, the packaging cell containing and expressing a nucleic acid encoding a mutant adenovirus E4orf6 protein as described above, (b) transfecting or infecting the packaging cell with a nucleic acid that encodes a recombinant viral vector selected from the group consisting of adenovirus vectors and adeno-associated virus vectors as described above (the vector preferably lacking a functional gene encoding E4orf6 protein);(c) culturing the transfected or infected cells under conditions that permit expression of the mutant E4orf6 protein and the production of packaged recombinant viral vector therein; and then (d) collecting packaged recombinant viral vector from said cultured cells.

Any type of cell may be used as the packaging cell or host cell, but mammalian cells typically used in the production of adenovirus or AAV vectors, such as the 293 human embryonic kidney cell or the 911 human cell line (see, e.g., F. Fallaux et al., *Hum. Gene Ther.* 7, 215–222 (1996)), are preferred. The packaging cell may be transiently or stably transfected with nucleic acid encoding the mutant adenovirus E4orf6 protein (e.g., by electroporation of a plasmid containing a construct that expresses the mutant adenovirus E4orf6 protein therein). By "stably transfected" or stable growth of the cell line is meant that the cell may be grown in culture for at least one or two months while maintaining expression of the mutant protein. In the alternative, the packaging cell may be infected with a virus such as an adenovirus that contains and expresses the mutant E4orf6 protein in the packaging cell. Suitable cell lines, along with techniques for transfection, infection, culturing and collecting steps, are all well known to those skilled in the art. See, e.g., U.S. Pat. Nos. 5,604,090 to Alexander et al., U.S. Pat. No. 5,658,776 to Flotte et al., U.S. Pat. No. 5,693,531 to Chlorini et al., U.S. Pat. No. 5,837,484 to Trempe et al., U.S. Pat. No. 5,945,335 to Colosi, U.S. Pat. No. 6,001,650 to Colosi, U.S. Pat. No. 6,037,177 to Snyder, and U.S. Pat. No. 6,040,183 to Ferrari et al., the disclosures of which are to be incorporated by reference herein in their entirety.

The viral vectors and packaging cell lines may incorporate E2b region deletions as described in U.S. Pat. No. 6,063,622 to Chamberlain and Amalfitano.

Mutant E4orf6 proteins of the present invention may also be produced in accordance with standard techniques and used to enhance efficiency of transduction by a recombinant AAV virus, as described in U.S. Pat. No. 5,756,283.

The examples set forth below demonstrate which molecular features of the arginine-faced, amphipathic α helix are required for a functional interaction with the E1B-55 kDa protein and support a productive viral infection. The hydrophilic face of this α helix contains six arginine residues. Replacement of these arginine residues with the similarly charged lysine residue had little effect on the interaction with the E1B-55 kDa protein in cells. Two arginine residues, at position 241 and 243, were found to be critical for a functional E4orf6-E1B-55 kDa protein interaction. These residues lie on opposite sides of the α helix. The other four arginine residues comprise a central region of the α helix that requires a net positive charge to preserve the ability to direct the nuclear localization of the E1B-55 kDa protein. The features of the amphipathic, arginine-faced α helix required for interaction with the E1B-55 kDa protein in cells differs from those required for E4orf6 protein function during a productive Ad infection. Some E4orf6 variants that failed to direct the E1B-55 kDa protein to the nucleus provided wild-type function during productive Ad infection. However, an E4orf6 variant that retained the E1B-55 kDa protein within the nucleus and therefore resembled the wild-type protein by this assay, failed to supply E4orf6 protein function during Ad infection. These results indicate that the ability of the E4orf6 protein to relocalize the E1B-55 kDa protein to the nucleus can be separated from the ability of the E4orf6 protein support a productive infection. In turn, this suggests that the interactions between the E4orf6 and E1B-55 kDa proteins is necessary to direct nuclear localization of the E1B-55 kDa protein and may differ from those required during productive Ad infection. The separation of these functions in the mutant proteins described here may reflect a diverse number of interactions that are mediated by the amphipathic arginine-faced α helix of the E4orf6 protein for the many functions of this protein.

In the following examples, hrs means hours, Ad means adenovirus, orf means open reading frame, CsCl means cesium chloride, μg means microgram, kDa means kilo-Dalton, bp means base pair, kbp means kilo-base pair, M means Molar, mM means milli-Molar, min means minute, SDS-PAGE means sodium dodecyl sulfate-polyacrylamide gel electrophoresis, kcal means kilo-calorie, ° C. means degrees Celsius, K means Kelvin, mm means millimeter, PFU means plaque forming units, mL means milliliter, dpi means dots per inch, and Å means Angstrom.

EXAMPLE 1

Materials and Methods

Cell culture and viruses. Cell culture media, cell culture supplements and serum were obtained from Life Technologies (Gaithersburg, Md.) through the Tissue Culture Core Laboratory of the Comprehensive Cancer Center of Wake Forest University. HeLa and W162 cells (Weinberg and Ketner (1983) *Proc. Natl. Acad. Sci. USA* 80:5383–5386) were maintained in Dulbecco-modified Eagle's minimal medium (DMEM) supplemented with 10% newborn calf serum as previously described (Goodrum and Ornelles (1997) *J. Virol.* 71:548–561). Two strains of HeLa cells were used in this work. The "faster growing" strain of HeLa cells (CCL2.2) was obtained from the American Type Culture Collection in the late 1980s. This strain exhibits the more typical morphology and growth rate (doubling time=20 hrs) of adherent HeLa cells. Another variant of HeLa cells that had been propagated in lab of T. Shenk for a longer period of time is identified as a "slower growing" strain of HeLa cells. The doubling time of this HeLa cell strain is approximately 36 hrs. This slower growing strain of HeLa cells reaches confluence at a lower cell density compared to the faster growing strain of HeLa cells, consistent with a more spread, less cuboidal morphology.

dl309 served as the wild-type Ad5 used in these studies. dl309 lacks a portion of the E3 region, which has been shown to be dispensable for growth in culture (Jones and Shenk (1979) *Cell* 17:683–689). The E4-deletion virus, dl1014, was constructed by Bridge and Ketner and described previously ((1989) *J. Virol.* 63:345–353). This virus is able to express only the orf4 protein from the E4 region. The wild-type virus, dl309, was propagated in 293 cells (Graham et al. (1977) *J. Gen. Virol.* 36:59–74) and dl1014 propagated in W162 cells (Weinberg and Ketner (1983) *Proc. Natl. Acad. Sci. USA* 80:5383–5386). Virus stocks were prepared by sequential centrifugation through CsCl as described previously (Goodrum and Ornelles (1997) *J. Virol.* 71:548–561).

The recombinant vaccinia virus used to express the T7 RNA polymerase, vTF7.3, was created by Fuerst et al. ((1986) *Proc. Natl. Acad. Sci. USA* 83:8122–8126). Expression of the E1B-55 kDa and E4orf6 genes from the T7 promoter was achieved as described previously (Goodrum et al. (1996) *J. Virol.* 70:6323–6335). Briefly, cells were infected with vTF7.3 in reduced serum medium and transfected with 1 µg plasmid DNA mixed with 3 µg Fugene 6 as per the manufacturer's (Roche, Nutley, N.J.) recommendation. Cells were analyzed by immunofluorescence between 12 and 14 hrs after infection/transfection.

Plasmids and site-directed mutagenesis. The plasmids carrying the E4orf6 and E1B-55 kDa genes were described previously (Goodrum et al. (1996) *J. Virol.* 70:6323–6335; Orlando and Ornelles (1999) *J. Virol.* 73:4600–4610). Most E4orf6 variants were created by site-directed mutagenesis using the polymerase chain reaction (PCR) (Boles and Miosga (1995) *Curr. Genet.* 28:197–198; Sarkar and Sommer (1990) *Biotechniques* 8:404-407). Briefly, arginine codons were changed by performing PCR with a 5' oligonucleotide primer containing the altered E4orf6 sequences and a 3' primer corresponding to sequences beyond the 3' end of the E4orf6 coding region (Table 1). The resulting PCR product of approximately 150 bp was used with an oligonucleotide corresponding to sequences beyond the 5' end of the E4orf6 coding region to perform a second PCR synthesis (. The resulting 1 kbp fragment containing the intended mutation was subcloned into pGem 11z (Promega, Madison, Wis.) by standard means. The R4K and $Arg_{241, 243, 244, 248}Ala$ E4orf6 variants were created using the $Arg_{241}Pro, Val_{250}Ser$ variant described previously (Orlando and Ornelles (1999) *J. Virol.* 73:4600–4610). Restriction digestion of $Arg_{241}Pro, Val_{250}Ser$ cDNA with NruI and StuI removes a blunt-ended, 30 bp DNA fragment encoding amino acids 241 through 250 of the E4orf6 protein. A 30 base oligonucleotide encoding the desired changes and its complement were annealed and ligated into the digested $R_{241}P, V_{250}S$ cDNA to introduce the desired changes. The mutations in the E4orf6 gene were verified by restriction analysis and confirmed by automated DNA sequencing of approximately 600–800 bp of the construct through the DNA Sequencing and Gene Analysis Core Laboratory of Wake Forest University. A list of the mutagenic oligonucleotides with the diagnostic restriction sites used in this are listed in Table 2. For expression from an intrinsically active promoter, certain E4orf6 variant cDNAs were subcloned into the pCMV Neo-BamHI vector (Baker et al. (1990) *Science* 249:912–915) by standard means.

TABLE 1

E4orf6 mutagenic strategy

| E4orf6 variant | Mutagenic oligos used |
|---|---|
| $R_{240}E$ | do120 |
| $R_{241}E$ | do121 |
| $R_{243}E$ | do41 |
| $R_{244}E$ | do42 |
| $R_{248}E$ | do122 |
| $R_{251}E$ | do123 |
| $R_{240,241}E$ | do37 |
| $R_{243,244}E$ | do39 |
| $R_{248,251}E$ | do38 |
| $R_{240,251}E$ | do120 + do123 |
| $R_{240}A$ | do130 |
| $R_{241}A$ | do161 |
| $R_{243}A$ | do136 |
| $R_{244}A$ | do162 |
| $R_{248}A$ | do163 |
| $R_{251}A$ | do131 |
| $R_{240,241}A$ | do127 |
| $R_{243,244}A$ | do128 |
| $R_{248,251}A$ | do129 |
| $R_{240,251}A$ | do130 + do131 |
| $R_{240,244,251}A$ | do130 + do131 + do138 |
| $R_{240,248,251}A$ | do130 + do131 + do139 |
| $R_{240,244,248,251}A$ | do130 + do131 + do138 + do167 |
| $R_{241,243,244,248}A$ | do112 + do113 |
| $R_{241,243,244,248}K$ (R4K) | do114 + do115 |

TABLE 2

List of E4orf6 mutagenic oligos

| Oligo | Sequence (5'–3') | | Amino acid change | Diagnostic, comments |
|---|---|---|---|---|
| do37 | CGCTG CTGTG CCGAG GAGAC AAGGC GCCT | (SEQ ID NO:1) | 240, 241 to E | |
| do38 | CGCCT TATGC TGGAG GCGGT GGAAA TCATC GCTGA | (SEQ ID NO:2) | 248, 251 to E | |
| do39 | GCCCG GAGGA CAGAG GAGCT TATGC TGCGG | (SEQ ID NO:3) | 243, 244 to E | |

TABLE 2-continued

List of E4orf6 mutagenic oligos

| Oligo | Sequence (5'–3') | | Amino acid change | Diagnostic, comments |
|---|---|---|---|---|
| do41 | GCCCG GAGGA CAGAG CGCCT TATGC TG | (SEQ ID NO:4) | 243 to E | |
| do42 | CGGAG GACAA GGGAG CTTAT GCTGC GG | (SEQ ID NO:5) | 244 to E | |
| do112 | GCAAC GGCAG CGCTC ATGCT AGCAG CGGTG | (SEQ ID NO:6) | 241, 243, 244, 248 to A | Nhe I, pair with do113 |
| do113 | CACCG CTGCT AGCAT GAGCG CTGCC GTTGC | (SEQ ID NO:7) | 241, 243, 244, 248 to A | Nhe I, pair with do112 |
| do114 | AAGAC CAAGA AGCTT ATGCT GAAGG CAGTA | (SEQ ID NO:8) | 241, 243, 244, 248 to K | Hind III, pair with do115 |
| do115 | TACTG CCTTC AGCAT AAGCT TCTTG GTCTT | (SEQ ID NO:9) | 241, 243, 244, 248 to K | Hind III, pair with do114 |
| do120 | GGTGC GCTGC TGCGC AGAGA GGACA AGGCG | (SEQ ID NO:10) | 240 to E | Fsp I |
| do121 | GCTGC TGTGC CCGGG AGACA AGGCG CCTTA T | (SEQ ID NO:11) | 241 to E | Sma I |
| do122 | GGCGC CTTAT GCTCG AGGCG GTGCG AATC | (SEQ ID NO:12) | 248 to E | Xho I and Ava I |
| do123 | GCTGC GGGCG GTCGA AATCA TCGCT GAGG | (SEQ ID NO:13) | 251 to E | Taq I |
| do127 | GGTGC GCTGC TGTGC AGCTG CGACA AGGCG CCTTA TG | (SEQ ID NO:14) | 240, 241 to A | Pvu II |
| do128 | GCCCG GAGGA CAGCT GCCCT TATGC TGCGG | (SEQ ID NO:15) | 243, 244 to A | Pvu II |
| do129 | GGCGC CTTAT GCTGG CAGCT GTGGC AATCA TCGCT GAGGA G | (SEQ ID NO:16) | 248, 251 to A | Pvu II |
| do130 | GCGCT GCTGT GCCGC GCGCA CAAGG CGCCT TATG | (SEQ ID NO:17) | 240 to A | BssH II |
| do131 | GCTGC GGGCG GTCGC GATTA TCGCT GAGGA GACC | (SEQ ID NO:18) | 251 to A | Nru I |
| do136 | CCCGG AGGAC AGCGC GCCTT ATGC | (SEQ ID NO:19) | 243 to A | BssH II |
| do138 | CGCGC ACAAG AGCTC TTATG CTGC | (SEQ ID NO:20) | 244 to A in R240/51A | Sac I |
| do139 | CCTTA TGCTG GCGGC CGTCG CGATT ATC | (SEQ ID NO:21) | 248 to A in R240/51A | EagI |
| do161 | CTGCT GTGCC CGGGC GACAA GGCGC TTAT G | (SEQ ID NO:22) | 241 to A | Sma I |
| do162 | CCGGA GGACA AGGGC CCTTA TGCTG CGGGC | (SEQ ID NO:23) | 244 to A | Apa I |
| do163 | GGCGC CTTAT GCTGG CGGCC GTGCG AATCA TCG | (SEQ ID NO:24) | 248 to A | Eag I |
| do167 | GAGCT CTTAT GCTAG CGGCG GTCGC GATT | (SEQ ID NO:25) | 248 to A in R240/44/51A | |

Indirect immunofluorescence. Indirect immunofluorescence and photomicroscopy of whole cells was conducted as previously described (Ornelles and Shenk (1991) *J. Virol.* 65:424–429). Double label immunofluorescence was performed with the mouse monoclonal antibody, MAb3, (Marton et al. (1990) *J. Virol.* 64:2345–2359) which is specific for the amino terminus of the E4orf6 protein and the rat monoclonal antibody, 9C10, (Oncogene Science, Uniondale, N.Y.) (Zantema et al. (1985) *Virology* 142:44–58)) which is specific for the Ad5 E1B-55 kDa protein. The secondary antibodies were multiple-label-qualified goat antibodies conjugated to fluorescein and Rhodamine Red-X™ (Jackson ImmunoResearch, West Grove, Pa.). Samples were examined with a Leitz Dialux 20 EB microscope fitted for epifluorescent illumination and photographed using TMax film developed to an exposure index of 1600 ASA (Eastman Kodak, Rochester, N.Y.).

A "double blind" approach was used to quantify the degree of nuclear localization of the E1B-55 kDa protein. For this, the appropriate mixture of plasmids were prepared in randomly encoded tubes. A second investigator performed the infection/transfection using a randomly-labeled culture of cells. The presence of both E4orf6 and E1B-55 kDa protein was verified by double-label immunofluorescence as described above and the localization of the E1B-55 kDa protein scored as either cytoplasmic or nuclear as described in the Example 2. At least one hundred cells were scored for each sample.

Protein expression. Replicate cultures of infected and transfected cells were collected, resuspended in urea sample buffer (7.5 M urea, 50 mM Tris [pH 6.8], 1% SDS, 50 mM DTT, 5% β-mercaptoethanol, 0.05% bromophenyl blue), sonicated and heated for 10 min at 65° C. The proteins were separated by SDS-PAGE, electrophoretically transferred to nitrocellulose, and the E4orf6-related proteins and the E1B-55 kDa protein visualized by immunoblotting using MAb3 (Marton et al. (1990) *J. Virol.* 64:2345-2359) and 2A6 (Sarnow et al. (1982) *Virology* 120:510-517), respectively, a secondary antibody conjugated to horseradish peroxidase (Jackson ImmunoResearch), and chemiluminescence detection (Pierce, Rockford, Ill.).

Sequence analysis and molecular modeling. Sequence analysis and secondary structure prediction was performed with the suite of programs available as the Wisconsin Package Version 10.1 (Genetics Computer Group, Madison, Wis.) Molecular models of the amphipathic α helix were analyzed by the Sybyl suite of programs (Tripos Associates, Inc., St. Louis, Mo.). The Composer module was used to assemble peptide models corresponding to residues 239 through 255 of the E4orf6 protein and related variants. The amino- and carboxy-terminus of the model was blocked with neutral blocking groups and all hydrogen atoms and unpaired electrons were added. Atomic charges were assigned from the Amber 95 model provided by Tripos Associates, Inc., and the peptide backbone was constrained to a standard α helix. Electrostatic effects were introduced with a dielectric constant that varied with interatomic distance and the model was energetically minimized by a reiterative process until the energy change per step was less than 0.02 kcal per mole. The Dynamics module was used to identify energetically reasonable configurations for the amino acid side chains by simulating exposure to 300 K for 8 picoseconds. The initial velocities of the atoms in the model were randomized between repeated simulations to sample the variety of allowable configurations. This repeated analysis with different initial conditions confirmed that the simulation parameters allowed all non-constrained atoms to reach dynamic equilibrium. The resulting structures were again minimized before using the MOLCAD module to project the electrostatic potential onto the solvent accessible surface of the peptide models.

Complementation analysis. HeLa cells were infected with dl309 (Jones and Shenk (1979) *Cell* 17:683-689) or dl1014 (Bridge and Ketner (1989) *J. Virol.* 63:631-638) and simultaneously transfected with the E4orf6 variant cDNA constructs analyzed in FIG. 7. For these experiments, 4×10$^5$ cells in a 65 mm dish were exposed to 1 μg of plasmid DNA, 3 μg of Fugene 6, and 4×10$^6$ PFU of virus in a 2 mL volume of OptiMEM (Life Technologies). After 6 hrs at 37° C., the virus and plasmid mixture was replaced with normal growth medium. Detailed methods for Adenovirus plaque assays have been described elsewhere (Jones and Shenk (1978) *Cell* 13:181-188). In brief, virus was harvested from HeLa cells by multiple cycles of freezing and thawing. The cell lysates were clarified by centrifugation and serially diluted for infection of W162 cells (Weinberg and Ketner (1983) *Proc. Natl. Acad. Sci USA* 80:5383-5386) grown in 6-well tissue culture dishes for plaque assays. Typically, valid data were collected from three dilutions in each series of dilutions. The virus yield was determined by linear regression and expressed as the number of plaques per mL of initial lysate.

Computer aided graphics. Film used to record chemiluminescence and immunofluorescence micrographs were scanned at 300 and 600 dpi, respectively, cropped with Photoshop 5.5 (Adobe Systems, Inc., San Jose, Calif.) and assembled with Canvas 5.1 and 7.0 (Deneba, Miami, Fla.) operating on a Macintosh microcomputer. Images produced by the Sybyl suite of programs were generated as 16-bit RGB files, transported to a Macintosh microcomputer as 8-bit RGB files, recolored with Photoshop 5.5 and saved as 8-bit CMYK images.

EXAMPLE 2

Arginine Residues In The Amphipathic α Helix Between Position 239 and 251 Form A Positively Charged Surface-Exposed Domain Using circular dichroism spectroscopy, Orlando and Ornelles previously demonstrated that a peptide corresponding to amino acids 239 through 254 of the 294 residue E4orf6 protein can exist as an amphipathic, arginine-faced α helix (Orlando and Ornelles (1999) *J. Virol.* 73:4600-4610). Variants of the E4orf6 protein that lack residues 241 through 250 or contain a proline in this region were defective. These mutant proteins failed to retain the E1B-55 kDa protein in the nucleus when expressed by transfection in non-infected cells and these mutant proteins failed to promote replication of an E4deletion virus when expressed by transfection in infected cells.

Figure 1:
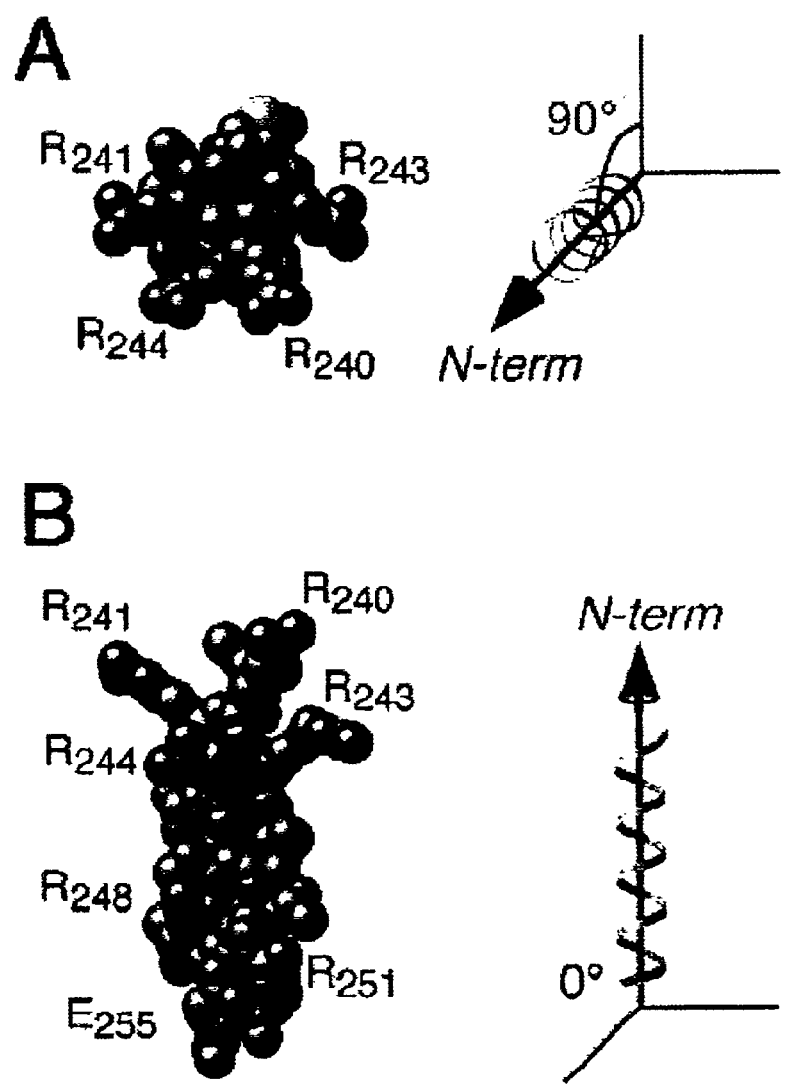
FIG. 1 (Parts A–B) shows a representation of the amphipathic arginine-faced α helix. Amino acids 239 through 255 of the E4Orf6 protein were modeled as an α helix by constraining the Cα carbons to a standard α helix. The side chains were allowed to adopt an energetically reasonable configuration using molecular dynamics as described in the Example 1. The identity of each atom is indicated by color: nitrogen=blue, carbon=gray, oxygen=red, sulfur=yellow. Hydrogen atoms are not shown. The lone pair of electrons associated with the sulfur is shown in green. Atoms in the peptide backbone are rendered in a muted color. The charged residues that are visible are labeled near the side chain. (A) View down the helix axis (N-terminus to C-terminus). (B) View of the hydrophilic face.

To identify features of this region that underlie the functional interaction between the E4orf6 and E1B-55 kDa proteins, a molecular model of the α helix was generated. The space-filling model in FIG. 1 illustrates the 4.7 turns of the α helix and a potential arrangement of residues 239 through 255 of the E4orf6 protein. In this model, the peptide backbone was constrained to a standard α helix and the side chains were allowed to adopt an energetically favored configuration using molecular dynamics as described in the Example 1. The amphipathic nature of this structure is evident when viewed down the helix axis (FIG. 1A). Arginine-241 and arginine-243 occur at the extreme sides of the hydrophilic face. The only non-aliphatic residues in the hydrophobic backbone of the α helix are threonine-242 and methionine-246. A likely distribution of the charged residues can be seen in the view of the α helix seen in FIG. 1B. Arginine-240, arginine-244 and arginine-248 align on the hydrophilic face over three turns of the α helix (FIG. 1B). In repeated modeling efforts, arginine-251 established a bond with the glutamic acid residue at position 255. Although it is unclear if the protein adopts an alpha-helical configuration beyond alanine-249 (Orlando, unpublished observation), the pair of electronegative glutamic acid residues at positions 255 and 256 (which is beyond the region modeled), seem likely to promote an interaction with the guanidinium group of arginine-251 irrespective of the surrounding secondary structure. Therefore, the arginine-251 may form an ionic bond with glutamic acid-255. Because the structure of the E4orf6 protein is not known, it is impossible to incorporate the influence of other more distal regions of the E4orf6 protein into the conformation of this region. Nonetheless, in the absence of such influences, it appears that the remaining five arginines are free to adopt a wide variety of configurations. This property would be consistent with their position on the solvent exposed face of this amphipathic α helix and would permit a significant degree of flexibility in binding diverse partners. These arginine residues may form a flexible positively charged or basic region on the surface of the E4orf6 protein.

To determine whether the identity of these six arginine residues or the basic nature of these residues is critical for E4orf6-E1B-55 kDa protein interaction, an E4orf6 variant, R4K, bearing four lysine substitutions was created and tested for a functional interaction with the E1B-55 kDa protein (FIG. 2A). The R4K and wild-type E4orf6 proteins were expressed with the E1B-55 kDa protein in HeLa cells using the vaccinia virus/T7 RNA polymerase infection-transfection expression system. The ability of the R4K protein to retain the normally cytoplasmic E1B-55 kDa protein in the nucleus was determined by double label immunofluorescence. Representative images from two independent experiments are shown in FIG. 2B. As previously reported, the E4orf6 protein is diffusely distributed throughout the nucleus and is excluded from the nucleoli (Orlando and Ornelles (1999) *J. Virol.* 73:4600–4610; Goodrum et al. (1996) *J. Virol.* 70:6323–6335). Although the E1B-55 kDa protein has been reported to shuttle between the cytoplasm and nucleus (Kratzer et al. (2000) *Oncogene* 19:850–857), this protein localizes primarily to the cytoplasm of transfected cells (FIG. 2B, second row). However, the subcellular localization of the E1B-55 kDa protein is changed upon coexpression with the E4orf6 protein (Goodrum and Ornelles (1999) *J. Virol.* 73:7474–7488). The E4orf6 protein retains the E1B-55 kDa protein in the cell nucleus. In most cells expressing both of these adenoviral proteins (FIG. 2B, third row), staining for the E1B-55 kDa protein appeared coincident with staining for the E4orf6 protein.

Like the E4orf6 protein, the R4K variant is found in the nucleus and retains a portion of the E1B-55 kDa protein in the nucleus of cells expressing both proteins. In contrast to the wild-type E4orf6 protein, the R4K protein appeared to be less efficient at retaining the E1B-55 kDa protein in the nucleus. In the example shown (FIG. 2B, fourth row), more cytoplasmic staining is evident for E1B-55 kDa protein in the presence of the R4K protein than in the presence of the wild-type E4orf6 protein (FIG. 2B, third row). Although the R4K protein retained at least a portion of the E1B-55 kDa protein in the nucleus in every cell examined, approximately 40% of these cells contained brighter staining for the E1B-55 kDa protein in the cytoplasm than in the nucleus. Nonetheless, since expression of the R4K protein induced the nuclear co-localization of at least a portion of the E1B-55 kDa protein in all cells, we conclude the basic charge of the arginine residues within the amphipathic α helix contributes to the functional interaction between the E4orf6 and E1B-55 kDa proteins.

The diminished ability of the R4K variant to retain the E1B-55 kDa protein in the nucleus is not due to reduced levels of the R4K protein. The steady-state level of the E4orf6, R4K, and E1B-55 kDa proteins in HeLa cells was determined by immunoblot. The amount of E4orf6 protein measured in cells expressing the E4orf6 protein alone or with the E1B-55 kDa protein was similar to the amount of R4K protein (FIG. 2C). Neither the E4orf6 protein nor the R4K variant affected the steady state level of the E1B-55 kDa protein. An equivalent amount of E1B-55 kDa protein was detected in lysates derived from cells expressing the E1B-55 kDa protein alone, the E1B-55 kDa and E4orf6 proteins, or the R4K and E1B-55 kDa proteins. Finally, none of the adenoviral proteins were detected in samples that were not transfected with the respective cDNA (FIG. 2B and FIG. 2C).

EXAMPLE 3

The Basic Nature of Arginines 241 and 243 is Required for E4orf6-E1B-55 Kda Protein Interaction To determine the significance of the positive charge at positions occupied by arginines for the E4orf6-E1B-55 kDa protein interaction, a collection of single arginine to glutamic acid replacement variants was created. These variants were tested for their ability to retain the E1B-55 kDa protein in the nucleus. The E4orf6 variants were expressed with the E1B-55 kDa protein by the vaccinia virus T7/RNA polymerase infection-transfection system and the localization of both proteins determined by double-label indirect immunofluorescence.

Figure 3:
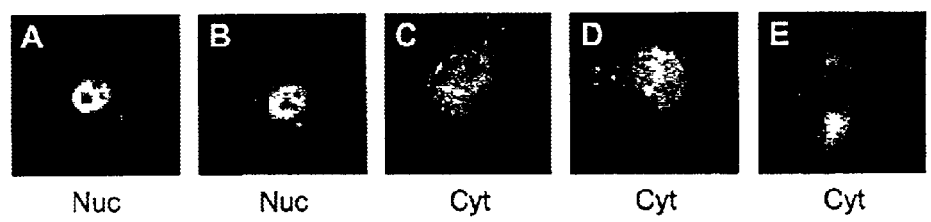
FIG. 3 (Parts A–E) shows the degree of E1B-55 kDa nuclear localization in cells expressing the $R_{240}E$ variant varies from cell to cell. Expression of the $R_{240}E$ E4orf6 variant and the E1B-55 kDa protein was established and the localization of the E1B-55 kDa protein determined as described in the legend to FIG. 2. The E1B-55 kDa protein was visualized with the rat monoclonal antibody 9C10. The localization represented in (A) and (B) was seen in 55% of the cells and was scored as nuclear. The uniform distribution represented in (C) was seen in only 4% of the cells and the predominantly cytoplasmic localization seen in (D) and (E) was seen in 46% of the cells. The uniform and cytoplasmic distributions were scored as cytoplasmic.

In most cells expressing both $R_{240}E$ and E1B-55 kDa proteins, at least a portion of the E1B-55 kDa protein was detected in the nucleus (FIG. 3A and FIG. 3B). However, like the R4K variant, the $R_{240}E$ variant was not as efficient as the wild-type E4orf6 protein at retaining the E1B-55 kDa protein in the nucleus. Indeed, none of the E4orf6 variants created in this study directed nuclear localization of the E1B-55 kDa protein as effectively as the wild-type E4orf6 protein. This property was quantified by the double-blind assay discussed below and seen in FIG. 5. The basis for this assay is illustrated by the representative images showing the localization of the E1B-55 kDa protein in the presence of the $R_{240}E$ variant (FIG. 3). This series of micrographs illustrates varying degrees to which the $R_{240}E$ mutant protein retained the E1B-55 kDa protein in the nucleus. More than half of the cells expressing both E1B-55 kDa and $R_{240}E$ proteins showed predominantly nuclear staining for the E1B-55 kDa protein (FIG. 3A and FIG. 3B). In slightly less than half of the cells, the E1B-55 kDa protein appeared to be predominantly restricted to the cytoplasm (FIG. 3D and FIG. 3E). The more uniform distribution of E1B-55 kDa protein (FIG. 3C) was observed in fewer than 4% of the cells.

In four independent experiments, the localization of the E1B-55 kDa protein was determined in a total of approximately 400 HeLa cells expressing both E1B-55 kDa and $R_{240}E$ proteins. An average of 55% of cells contained predominantly nuclear E1B-55 kDa protein. By contrast, in a similar number of cells expressing both wild-type adenoviral proteins, every cell (>99.5%) contained the majority of the E1B-55 kDa protein in the nucleus. Nonetheless, although less efficient than the wild-type protein, the E4orf6 variant bearing a glutamic acid substitution for arginine at position 240 was able to direct nuclear localization of the E1B-55 kDa protein (FIG. 4A).

Figure 4:
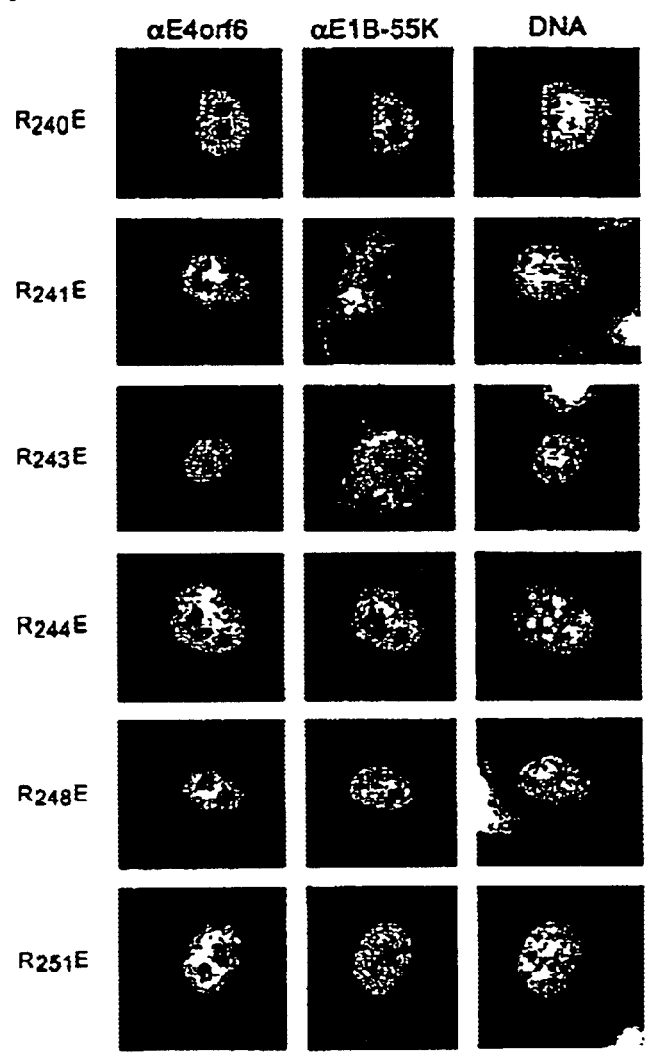
FIG. 4 (Parts A–B) shows E4orf6 variants with arginine to alanine replacement mutations at positions 241 or 243 do not retain the E1B-55 kDa protein in the cell nucleus after transfection. (A) Expression of the E4orf6-related proteins (indicated on the left) and the E1B-55 kOa protein was established, and the localization of the Ad proteins determined as described in the legend to FIG. 2. Representative images of a single cell from each transfection are presented with the E4orf6 protein shown in the left column (αE4orf6), E1B-55 kDa protein in the center column (αE1B-55K), and DNA visualized with DAPI in the right column (DNA). (B) In parallel with the samples prepared for immunofluorescence, expression of the E4orf6 and E1B-55 kDa proteins was established by transfection of the cDNAs indicated above each lane and the E4orf6-related proteins and the E1B-55 kDa protein were visualized by immunoblotting as described in the legend to FIG. 2.
Figure 4:
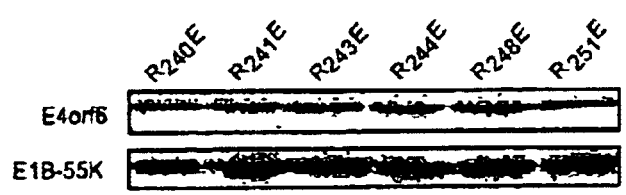
Figure 5:
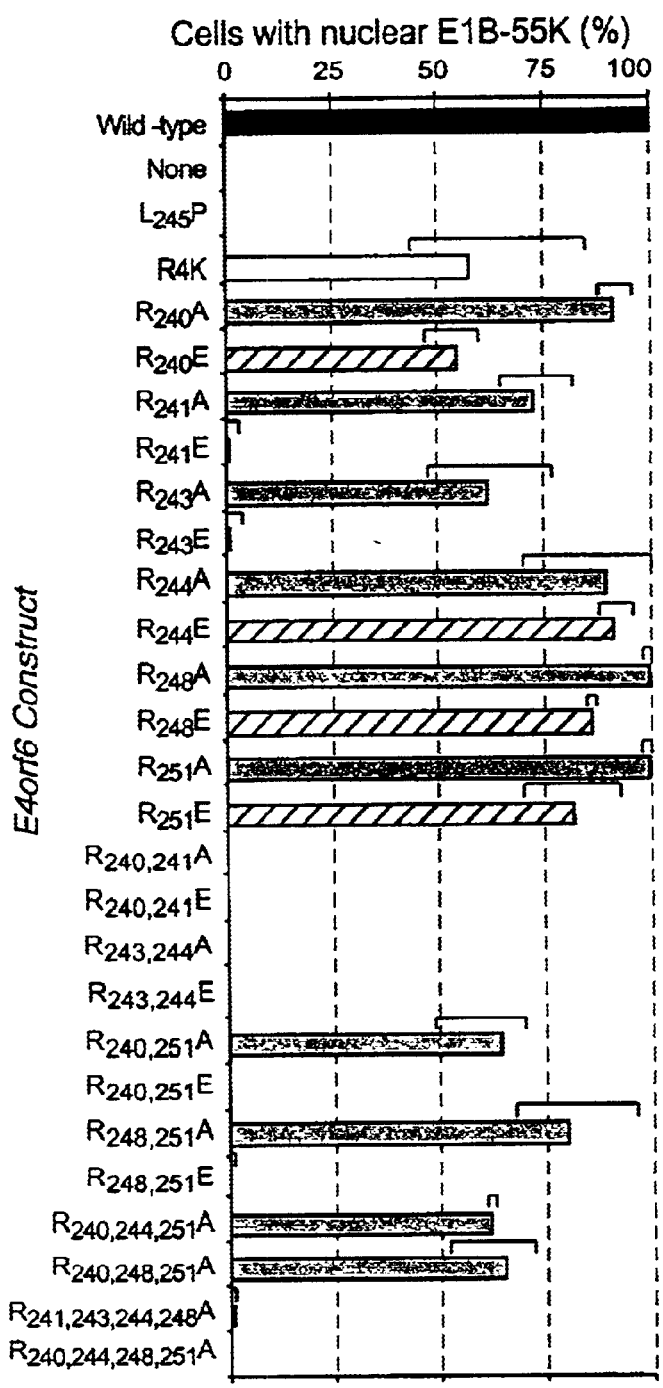
FIG. 5 shows E4orf6 variants bearing arginine replacement mutations within the amphipathic α helix fail to retain the E1B-55 kDa protein in the nucleus less effectively than the wild-type E4orf6 protein. Expression of the E4orf6-related proteins and the E1B-55 kDa protein was established in a blinded fashion. Using immunofluorescence, expression of the E4orf6 protein variant (indicated on left) was established and the localization of the E1B-55 kDa protein was determined in a blinded fashion as described in a the legend to FIG. 2 and in the Example 1. Approximately 100 cells expressing each E4orf6 variant and the E1B-55 kDa protein were evaluated in each of four independent experiments. The localization of the E1B-55 kDa protein was scored as nuclear or cytoplasmic as indicated in the legend to FIG. 3. Each bar represents the average fraction of cells containing predominantly nuclear E1B-55 kDa protein. The brackets above each bar indicate the minimum and maximum values measured in four experiments. The solid black bar represents the value measured for the wild-type E4orf6 protein, the solid white bar represents the R4K variant, the gray bars represent arginine to alanine replacement variants, and the hatched bars represent arginine to glutamic acid variants.

The mutant proteins $R_{244}E$, $R_{248}E$ and $R_{251}E$ directed nuclear localization of the E1B-55 kDa protein in a majority of cells (FIG. 4A). For each of these variants, approximately 85% of cells expressing both proteins contained predominantly nuclear E1B-55 kDa protein as seen in the representative examples in FIG. 4A. However, variants of the E4orf6 protein bearing arginine to glutamic acid amino acid replacement mutations at residues 241 or 243 failed to retain the E1B-55 kDa protein in the nucleus (FIG. 4A). Strikingly, fewer than 1% of cells expressing the E1B-55 kDa and either the $R_{241}E$ or $R_{243}E$ mutant protein contained the E1B-55 kDa protein in the nucleus (FIG. 5). Furthermore, the distribution of the E1B-55 kDa protein in this minority of cells was uniform, resembling that seen in FIG. 3C, thus further illustrating the defective nature of these mutant proteins. This result leads us to suggest that a positive charge at positions 241 and 243 is critical for a functional interaction with the E1B-55 kDa protein.

The diminished ability of the $R_{240}E$, $R_{244}E$, $R_{248}E$ and $R_{251}E$ variants to retain the E1B-55 kDa protein in the nucleus and the loss of this function in the $R_{241}E$ and $R_{243}E$ variants cannot be attributed to a gross change in localization nor to reduced levels of the E4orf6 variants. Each of the glutamic acid-substitution variants were distributed in the nucleus in a manner indistinguishable from the wild-type E4orf6 protein (compare FIG. 2B and FIG. 3A). Also note that although the amphipathic α helix has been suggested to function as one of two nuclear localization or nuclear retention signals encoded in the E4orf6 protein, the mutations introduced in this region of the protein in this study did not disrupt nuclear localization of the E4orf6 protein. Lysates of cells expressing the single arginine to glutamic acid variants and the E1B-55 kDa protein were analyzed by an immunoblot to determine the steady-state levels of the adenoviral proteins. All of these constructs expressed similar levels of E4orf6-related protein (FIG. 4B). Furthermore, expression of these variants did not affect the level of E1B-55 kDa protein (FIG. 4B). Thus, the interaction of the E4orf6 and E1B-55 kDa proteins measured by this co-localization assay is ablated by the $R_{241}E$ and $R_{243}E$ mutations, modestly reduced by the $R_{240}E$ mutation, and only slightly affected by the $R_{244}E$, $R_{248}E$ and $R_{251}E$ mutations.

To determine whether the acquisition of a negative charge or the loss of a positive charge at the position normally occupied by arginine disrupted the E4orf6-E1B-55 kDa protein interaction, single arginine to alanine variants were tested for their ability to retain the E1B-55 kDa protein in the nucleus. The ability of these, as well as all other mutant E4orf6 proteins to direct nuclear localization of the E1B-55 kDa protein was quantified by a double-blind approach. Cells expressing both the E4orf6 variant and the E1B-55 kDa protein were evaluated for the relative staining intensity of the E1B-55 kDa protein in the nucleus versus the cytoplasm. Those cells that contained stronger staining in the nucleus relative to the cytoplasm were scored as having a predominantly nuclear E1B-55 kDa protein. Each value plotted in FIG. 5 represents the average of four independent transfection/infections from two independent experiments. The ranges associated with each point indicate the minimum and maximum values of the four measurements.

The $R_{240}A$ variant retained the E1B-55 kDa protein in the nucleus of approximately 90% of cells expressing both proteins. This value was significantly greater than the 55% average measured for the $R_{240}E$ variant. Moreover, the lowest percentage of cells containing nuclear E1B-55 kDa protein in the presence of the $R_{240}A$ variant (88%) exceeded the maximum value measured in the presence of the $R_{240}E$ variant (62%). Therefore it seems likely that the acquisition of negative charge at position 240 in the $R_{240}E$ variant, rather than the loss of a positive charge at this position in the $R_{240}A$ variant, reduced the strength of interaction with the E1B-55 kDa protein.

Because E4orf6 variants that contained glutamic acid in positions 244, 248 or 251 behaved like the wild-type protein with respect to E1B-55 kDa nuclear retention, we expected that the corresponding arginine to alanine variants would also function like the wild-type protein. This was indeed observed. Cells expressing the E1B-55 kDa protein and either the $R_{244}A$, $R_{248}A$ or $R_{251}A$ mutant proteins contained predominantly nuclear E1B-55 kDa protein in 90% to 98% of the cells. By contrast, the $R_{241}A$ and $R_{243}A$ variants relocalized the E1B-55 kDa protein to the nucleus in 73% and 62% of the cells, respectively (FIG. 5). This intermediate value, although greater than that measured for the corresponding glutamic acid variants, is consistent with the notion that a positive charge at position 241 and 243 is important for the function of the E4orf6 protein. Further evidence in support of this idea can be derived from the ostensibly weaker interaction of the $R_{241}A$ and $R_{243}A$ proteins with the E1B-55 kDa protein seen in the slower growing strain of HeLa cells. In this strain of HeLa cells, the $R_{241}A$ and $R_{243}A$ mutant proteins relocalized the E1B-55 kDa protein in less than 20% of the cells whereas the other alanine substitution mutant proteins did so to the same extent as in the faster growing HeLa cell variant (data not shown).

The failure of the $R_{241}E$ and $R_{243}E$ variants and the diminished ability of the $R_{241}A$ and $R_{243}A$ variants to retain the E1B-55 kDa protein in the nucleus shows a requirement for a positively charged amino acid at positions 241 and 243 for this interaction with the E1B-55 kDa protein. Since the $R_{241}A$ and $R_{243}A$ variants can retain at least a portion of the total E1B-55 kDa protein in the nucleus, it is possible that a neighboring arginine residue may partially compensate for the loss of $R_{241}$ or $R_{243}$. Therefore, double arginine to alanine variants were created and tested for their ability to retain the E1B-55 kDa protein in the nucleus. An E4orf6 variant bearing arginine to alanine substitutions at positions 240 and 241 did not relocalize any E1B-55 kDa protein to the nucleus. Similarly, the $R_{243,244}A$ variant was completely defective in its ability to retain the E1B-55 kDa protein in the nucleus. By contrast, two variants that preserved arginine-241 and arginine-243, $R_{240,251}A$ and $R_{248,251}A$, retained the E1B-55 kDa protein in the nucleus of 70% and 82% of cells expressing both proteins, respectively. The properties of these double alanine-substitution variants provide further support for the importance of residues 241 and 243 for this functional interaction between the E1B-55 kDa and E4orf6 protein.

EXAMPLE 4

A Net Positive Charge Among Positions 240, 244, 248 and 251 is Required for E4orf6-E1B-55 Kda Protein Interaction Under physiological conditions, the arginine residues of the amphipathic α helix can form a positively charged surface that may underlie many functions of the E4orf6 protein. Arginine-241 and arginine-243 lie on opposite sides of the solvent exposed face of this α helix and are important for the functional interaction of the E4orf6 and E1B-55 kDa proteins in cells. Arginines-240, -244, -248, and -251 can form a colinear arrangement over nearly three turns of the α helical segment to present a positively charged surface. Although molecular modeling efforts suggest that arginine-251 may bind glutamic acid-255 (FIG. 1B) and therefore may not contribute to this colinear arrangement, we tested the contribution of these four arginine residues to the E4orf6E1B-55 kDa protein interaction. Variant E4orf6 proteins with multiple replacements of these four amino acids with either glutamic acid or alanine were tested for their ability to retain the E1B-55 kDa protein in the nucleus of cells transiently expressing both proteins. As previously discussed, E4orf6 variants containing two arginine to alanine replacement mutations ($R_{240,251}A$ and $R_{248,251}A$) retained a portion of the E1B-55 kDa protein in the nucleus. By contrast, substituting glutamic acid for arginine at these same positions ($R_{240,251}E$ and $R_{248,251}E$) ablated the E4orf6-E1B-55 kDa protein interaction (FIG. 5). These double glutamic acid-replacement variants appeared completely defective with respect to their ability to retain the E1B-55 kDa protein in the nucleus. The distribution of the E1B-55 kDa protein in cells expressing any of double arginine to glutamic acid E4orf6 variants resembled that observed in cells expressing the E1B-55 kDa protein alone.

Figure 2:
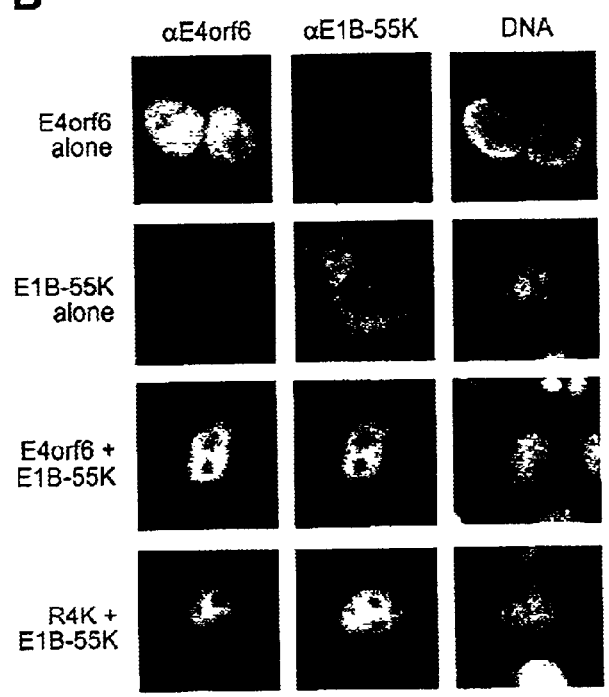
FIG. 2 (Parts A–C) shows an E4orf6 variant bearing arginine to lysine substitutions within the amphipathic a helix retains the E1B-55 kDa protein in the nucleus after transfection. (A) The amino acid sequence of the amphipathic a helix (E4orf6 residues 239–255, SEQ ID NO:26) and a variant showing amphipathic α helix the arginine to lysine substitutions at positions 241, 243, 244 and 248 (R4K, SEQ ID NO: 27). (B) Hela cells were infected with a recombinant vaccinia virus vTF7.3 to establish expression of the T7 RNA polymerase and then transfected with cONA under control of the T7 promoter to express the E4or6-related protein (left column) and the E1B-55 kDa protein (center column). The transfected cDNAs are identified on the left. Ad proteins were visualized by double-label immunofluorescence at 12 h after transfection and representative cells are shown. E4orf6 proteins were visualized with the mouse monoclonal antibody, MAb 3 (left column; αE4orf6), E1B-55 kDa protein was visualized with the rat monoclonal antibody, 9C10 (Zantema et al. (1985) *Virology* 142:44–58) (center column; αE1B-55K) and DNA was visualized with DAPI (right column; DNA). (C). In parallel with the samples prepared for immunofluorescence, expression of the E4orf6 and E1B-55 kDa proteins was established by transfection of the cDNAS indicated above each lane. Total cell protein was isolated 12 h after infection-transfection, separated by SDS-PAGE and transferred to a solid support. The E4orf6-related proteins and the E1B-55 kDa protein were visualized by immunoblotting with MAb 3 (MarIon et al. (1990) *J. Virol.* 64:2345-2359) and 2A6 (Salnow et al. (1982) *Virlogy* 120:510–517) respectively. Only the portion of the membranes containing the E4orf6-related proteins and the E1B-55 kDa proteins are shown.
Figure 2:
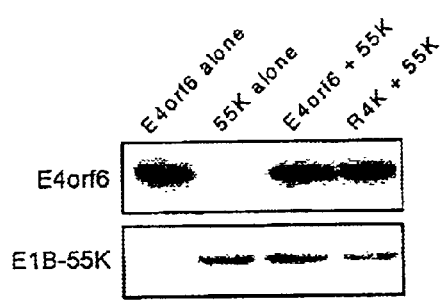

Unlike the double arginine to alanine variants, the double arginine to glutamic acid variants have a net neutral charge among these four central residues. Therefore, to test the possibility that the E4orf6-E1B-55 kDa protein interaction in transfected cells requires a net positive charge among these amino acids, cDNAs were created to express E4orf6 proteins containing triple or quadruple arginine to alanine replacement mutations. When co-expressed with the E1B-55 kDa protein, the $R_{240,244,251}A$ protein relocalized the E1B-55 kDa protein to the nucleus in 60% of the cells. Similar results were observed in cells expressing the $R_{240,248,251}A$ variant and the E1B-55 kDa protein. By contrast, the quadruple mutant protein, $R_{240,244,244,251}A$, failed to retain the E1B-55 kDa protein in the nucleus (FIG. 5). The localization of the E1B-55 kDa protein in these cells resembled that observed in cells expressing the E1B-55 kDa protein alone (FIG. 2). The quadruple alanine-substitution variant, $R_{240,244,244,251}A$, and the double glutamic acid-substitution variants, $R_{240,251}E$ and $R_{248,251}E$, have a net neutral charge among the four central residues. These results suggest that a positive surface on the hydrophilic face of the amphipathic α helix is required for E4orf6-E1B-55 kDa protein interaction in transfected cells.

Figure 6:
FIG. 6 (Parts A–G) shows E4orf6 variants that interact with the E1B-55 kDa protein are positively charged at the amino terminus of the amphipathic α helix. Amino acids 239 through 255 of E4orf6 protein variants were modeled as an α helix by constraining the positions of the Cα carbons to that of a standard α helix. The side chains were allowed to adopt an energetically reasonable configuration using molecular dynamics as described in the Methods. The solvent accessible surface of the model peptide was calculated and the electropositive potential of the molecule was projected onto this surface. The most electropositive regions are mapped to deep blue and the most negative regions mapped to bright red as indicated by the scale (kcal/mol e$^-$) (kilocalories per mole of electrons) on the right. The orientation of the a helical peptides is the same as seen in FIG. 1B where the amino-terminus is at the top and the hydrophilic face is exposed. The models and associated value for nuclear E1B -55 kDa protein retention (from FIG. 5) are (A) wild-type E4orf6 protein, 100%; (B) $R_{251}A$, 99%; (C) $R_{244}E$, 91%; (D) $R_{248,251}A$, 80%; (E) $R_{241}A$, 72%; (F) $R_{2402,244,251}A$, 62%; (G) $R_{241}E$, 0.8%.

Because the overall charge of the amphipathic α helix appears to be important for the ability of the E4orf6 protein to retain the E1B-55 kDa protein in the cell nucleus, molecular models of the amphipathic α helix of the various E4orf6 mutants were created and the theoretical charge density of these models were visualized (FIG. 6). The portion of the E4orf6 protein that was modeled was the same as that shown in FIG. 1 and includes alanine-239 through glutamic acid-255. As previously discussed, without knowing the three dimensional structure of the E4orf6 protein, it was not possible to incorporate effects of other portions of the E4orf6 protein on the conformation of the structure analyzed here. Therefore, for this analysis, the Cα atoms were constrained to the spacing of a standard α helix, with each residue separated by 100° and a rise of 1.5 Å. The amino acid side chains were allowed to adopt an energetically favored configuration after subjecting the model to the thermodynamic equivalent of 8 picoseconds at 300 K as described in the Example 1. This length of time was empirically determined to be sufficient for the side chains to reach a dynamic equilibrium and to establish any potential ionic interactions between side chains.

The orientation of the α helices modeled in FIG. 6 is the same as that of FIG. 1B where the amino-terminus is at the top and the hydrophilic face is exposed. These structures represent the solvent accessible surface of the model peptide. The electropositive potential of the molecule was projected onto this surface and is indicated by the scale bar in FIG. 6 where the most positive regions are mapped to deep blue and the most negative regions mapped to bright red. As expected, the positive charge of the multiple arginine residues in the wild-type structure (FIG. 6A) contributes to the overall positive nature (blue) of the amino-terminal portion of the α helix. The putative interaction between arginine-251 and glutamic acid-255 diminishes the contribution of both residues to the potential and that portion of the model is predicted to be nearly neutral.

The structures in FIG. 6 were arranged in rank order with respect to the ability of the corresponding mutant E4orf6 protein to retain the E1B-55 kDa protein in the nucleus. This ability was reported in FIG. 5 as the fraction of cells expressing both proteins with predominantly nuclear E1B-55 kDa. These values are approximately 100, 99, 90, 80, 70, 60 and 1 percent for the proteins represented by FIG. 6A through FIG. 6G, respectively. The pattern that emerges from this analysis reveals that the overall positive charge of the amino terminal portion of the amphipathic α helix is linked to the ability of the E4orf6 protein to retain the E1B-55 kDa protein in the nucleus. Although this pattern is not strictly observed, as can be seen comparing FIG. 6C and FIG. 6D, this trend was noted for all 26 of the mutant structures analyzed in this work (data not shown).

Collectively, these results suggest that the identity of the amino acids at positions 241 and 243 as well as the overall electropositive nature of the amino-terminus of the amphipathic α helix of the E4orf6 protein govern the interaction of the E4orf6 and E1B-55 kDa proteins as defined by co-localization in the nucleus during transient expression.

EXAMPLE 5

The Ability of the E4orf6 Protein to Direct Nuclear Localization of the E1B-55 kDa Protein is Not Strictly Linked to its Ability to Promote Virus Replication Previous work demonstrated that an intact amphipathic α helix is necessary for the E4orf6 protein to direct the E1B-55 kDa protein to the nucleus and for the E4orf6 protein to correct the growth defect of an E4-deletion virus (Orlando and Ornelles (1999) *J. Virol.* 73:4600–4610). Recently, Boyer and Ketner created a series of E4orf6 point mutants lacking conserved cysteine and histidine residues and observed a perfect correlation between the ability of the mutant protein to direct nuclear localization of the E1B-55 kDa protein, to co-immunoprecipitate with the E1B-55 kDa protein, and to stimulate late viral gene expression ((2000) *J. Biol. Chem.* 275:14969–14978). A similar correlation was observed by Weigel and Dobbelstein ((2000) *J. Virol.* 74:764–772). In addition, during an Ad infection, the E4orf6 protein directs the E1B-55 kDa protein to sites of viral RNA processing within the infected cell nucleus (Ornelles and Shenk (1991) *J. Virol.* 65:424–429). Thus, it seemed likely that the ability of the E4orf6 protein to function during a productive infection is linked to the ability of the E4orf6 protein to relocalize the E1B-55 kDa protein within the cell. The E4orf6 variants described here were somewhat impaired in their ability to retain the E1B-55 kDa protein in the nucleus. To determine if this limited ability of these mutant E4orf6 proteins to relocalize the E1B-55 kDa protein correlated with reduced function during Ad infection, eleven of the mutant E4orf6 proteins were tested for their ability to correct the growth defect of an E4deletion virus, dl1014, as previously described (Orlando and Ornelles (1999) *J. Virol.* 73:4600–4610). Surprisingly, the results described below demonstrate that the ability of the E4orf6 protein to retain the E1B-55 kDa protein in the nucleus is not strictly correlated with the ability of the protein to promote virus growth.

Two mutant E4orf6 proteins, $R_{241}A$ and $R_{243}A$, directed E1B-55 kDa nuclear localization less efficiently in the slower growing HeLa cell strain compared to the more rapidly growing HeLa cell strain. Therefore both of these HeLa cell strains were used for these complementation studies. The outcomes were largely independent of the HeLa cell variant used.

Figure 7:
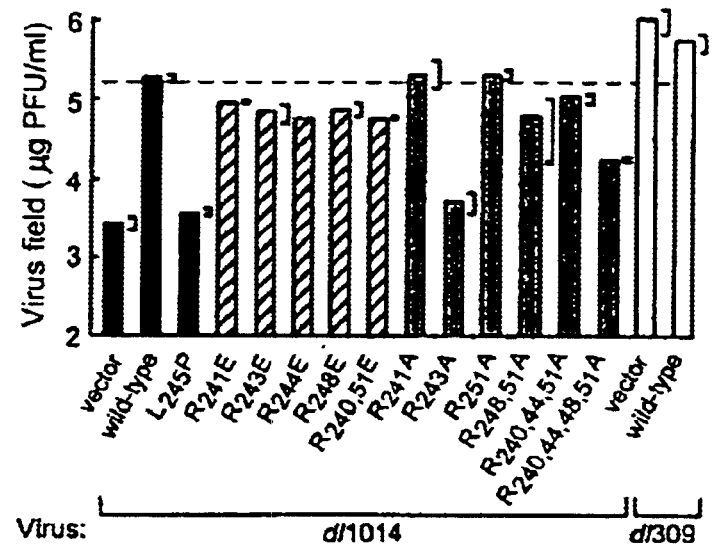
FIG. 7 (Parts A–B) shows the ability of the E4orf6 protein to retain the E1B-55 kDa protein to the nucleus is neither necessary nor sufficient to correct the growth defect of an E4-deletion virus. A "faster growing strain" of HeLa cells (A) and a slower growing strain" of HeLa cells (B) were infected with an E4-deletion virus lacking all E4 open reading frames except orf4, dl1014, or a phenotypically wild-type virus, dl309, at 10 PFU per cell and simultaneously transfected with cDNAs expressing the E4orf6-related constructs listed below each graph. The E4orf6-related proteins were expressed under the control of the major immediate-early promoter of CMV. Progeny virus was harvested after 48 hrs and quantified by plaque assay on the E4-complementing W162 cell line (Weinberg and Ketner (1983) *Proc. Nati. Acad Sci. USA* 80:5383–5386). A representative experiment (of three) showing the average amount of virus (expressed as PFU per milliliter of initial culture volume) obtained from two independent infections is shown. The range of virus recovered in the two independent infections is indicated by the brackets on the right.
Figure 7:
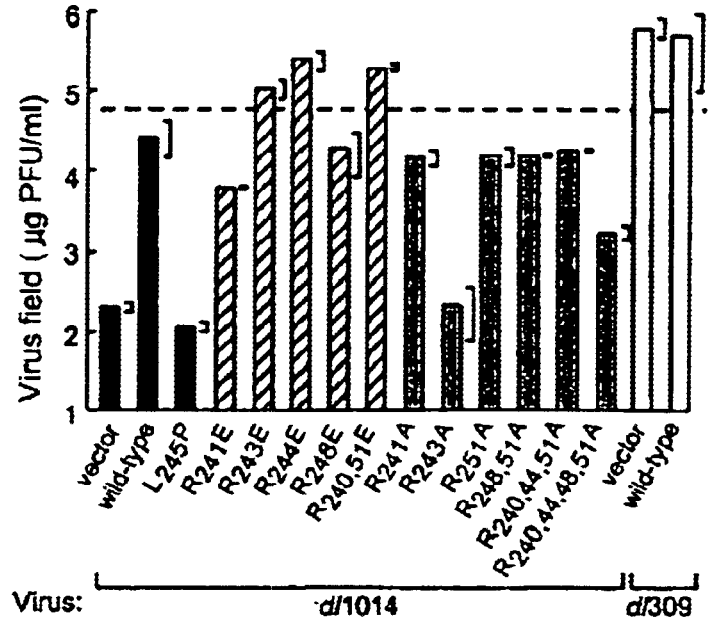

The phenotypically wild-type virus, dl309, replicated to equivalent levels in both HeLa cell strains. Expression of the wild-type E4orf6 protein did not affect growth of the wild-type virus (FIG. 7). The E4-deletion virus, dl1014, replicated to approximately to 3000-fold reduced levels compared to the wild-type virus in the slow growing HeLa cell strain and to approximately 300-fold reduced levels in the more rapidly growing HeLa cell strain (FIG. 7).

To measure the extent to which the mutant E4orf6 proteins correct the growth of the E4-deletion virus, HeLa cells were simultaneously infected with dl1014 and transfected with the appropriate E4orf6 cDNA expression constructs. Two days after infection/transfection, cells and growth media were collected and the amount of virus produced was quantified by plaque assay. As previously reported (Orlando and Ornelles (1999) *J. Virol.* 73:4600–4610), cells infected with dl1014 and simultaneously transfected with an empty vector or a vector expressing the defective $L_{245}P$ E4orf6 variant protein produced the same amount of virus as infected cells that were not transfected (FIG. 7 and data not shown). By contrast, cells infected with dl1014 and simultaneously transfected with a wild-type E4orf6 expression vector produced over 200-fold more virus. Evaluating similarly treated cells by immunofluorescence for expression of the E4orf6 protein, it was determined that the orf6 variant was expressed by transfection in 18±2% (average of 6 determinations±S.D.) of the rapidly growing HeLa cells (FIG. 7A) and 13±2% (average of 6 determinations±S.D.) of the slower growing HeLa cells (FIG. 7B). Therefore, if the transfected construct fully restored E4orf6 protein function, one would expect that the virus yield should be approximately 18% and 13% of the wild-type virus yield in the respective cell lines. These anticipated values are indicated by the dashed lines in FIG. 7. This anticipated value was measured for the rapidly growing HeLa cell strain (FIG. 7A). However, the yield of virus from the slow growing HeLa cell strain transfected with the wild-type orf6 construct was less than the expected value by a factor of approximately 3. The significance of this difference is uncertain but could be due to the variability associated with the measures of virus replication and transfection efficiency used here.

When infected with dl1014 and simultaneously transfected with the glutamic acid substitution variants $R_{241}E$, $R_{243}E$, $R_{244}E$, $R_{248}E$ and $R_{240,251}E$, the more rapidly growing HeLa cell strain produced nearly the same (2- to 3-fold reduced) amount of virus as dl1014-infected cells transfected with the wild-type construct (FIG. 7A). With the exception of $R_{241}E$, these same constructs promoted the replication of dl1014 to a greater or equivalent extent compared to the wild-type E4orf6 construct in the slower growing HeLa cell strain (FIG. 7B). Although not as effective as the wild-type E4orf6 protein in the slower growing HeLa cell strain, the $R_{241}E$ mutant protein enhanced replication of the E4-mutant virus by nearly 100-fold. The ability of the $R_{244}E$ and $R_{248}E$ variants to promote virus growth was expected because these E4orf6 variants behaved similarly to the wild-type protein with respect to altering E1B-55 kDa protein localization. However, three of these glutamic acid substitution variants, $R_{241}E$, $R_{243}E$ and $R_{240,251}E$, failed to retain the E1B-55 kDa protein in the nucleus and their near wild-type function in this complementation assay was unexpected. Thus, it appears that ability to promote virus growth can be dissociated from the property of directing E1B-55 kDa protein to the nucleus.

The alanine-substitution variants $R_{251}A$, $R_{248,251}A$ and $R_{240,244,251}A$ behaved as expected based on their ability to direct nuclear localization of the E1B-55 kDa protein. Each of these variants retained the E1B-55 kDa protein in at least 62% of HeLa cells transiently expressing both proteins (FIG. 5). When expressed by transfection in dl1014-infected cells, these variants corrected the growth of this virus nearly as well (within a factor of 3) as the wild-type E4orf6 protein.

However, the behavior of other alanine substitution variants analyzed by this method provide further support for the idea that virus growth enhancement can be dissociated from the property of E1B-55 kDa protein relocalization. The quadruple alanine-substitution variant, $R_{240,244,248,251}A$, failed to retain the E1B-55 kDa protein in the nucleus of over 400 cells evaluated that transiently expressed both proteins (FIG. 5). This E4orf6 variant restored the growth of dl1014 to 10% the level associated with the wild-type E4orf6 protein in the fast growing HeLa cell strain (FIG. 7A) and to 7% of the wild-type E4orf6-associated value in the slow growing HeLa cell strain (FIG. 7B). These values represent a 50- and 300-fold respective increase over the yield of virus from infected cells transfected with the empty vector. Therefore, this E4orf6 variant has an intermediate ability to correct the growth defect of dl1014.

Cells infected with dl1014 and simultaneously transfected with the $R_{241}A$ expression construct produced approximately the same amount of virus as dl1014-infected cells transfected with the wild-type E4orf6 construct. This was measured in both the fast growing HeLa cell strain (FIG. 7A) in which the $R_{241}A$ protein directed nuclear retention of the E1B-55 kDa protein in 73% of the cells (FIG. 5) and in the slow growing HeLa cell strain (FIG. 7B) in which this value was only 16% (data not shown). Thus for these alanine-substitution variants, the inability or reduced ability to direct nuclear retention of the E1B-55 kDa protein after transfection is not reflected in the ability of this variant to correct the growth defect of an E4-deletion virus.

In contrast to the partial function of the $R_{241}A$ protein during a virus infection, the $R_{243}A$ protein was defective with respect to virus growth even though by morphological criteria, the $R_{243}A$ variant resembled the $R_{241}A$ variant. The $R_{243}A$ variant directed nuclear retention of the E1B-55 kDa protein in 62% of the fast growing HeLa cells (FIG. 5) and in 17% of the slow growing HeLa cells (data not shown). However, both the fast growing and slow growing HeLa cell variants infected with dl1014 and simultaneously transfected with the $R_{243}A$ expression construct failed to produce any more virus than dl1014-infected cells transfected with an empty plasmid vector (FIG. 7A and FIG. 7B). Thus, although also preserving at least some ability to retain the E1B-55 kDa protein in the nucleus after transfection, the $R_{243}A$ protein appears to be unable to correct the growth defect of an E4-deletion virus. Together these results led to the conclusion that the ability to direct nuclear localization of the E1B-55 kDa protein is neither sufficient nor necessary to complement the growth of the E4-deletion virus, dl1014, under the conditions of these assays.

EXAMPLE 6

Key Features of the E4orf6 Amphipathic α Helix are Conserved Among Adenoviruses

To determine if the critical features of the arginine-faced amphipathic α helix of the E4orf6 protein are conserved among different adenoviruses, the predicted sequences of five human adenovirus E4orf6 proteins and three non-human adenovirus E4orf5 proteins that are similar to the human Ad E4orf6 protein were compared. The possibility that the protein adopts an α helical conformation at the carboxy terminus in each of these proteins was confirmed by the secondary structure prediction algorithm of Chou and Fassman ((1978) *Annu. Rev. Biochem.* 47:251–276). These proteins exhibited overall identity to the Ad2/5 E4orf6 protein ranging from 62% (human Ad17) through 24% (bovine Ad3). The fraction of identical amino acids in the predicted α helix region (Ad2/5 residues 239 through 255) also varied in a similar manner, from 88% (human Ad17) to 6% (bovine Ad3). The alignment of these sequences reveals that the critical features of the amphipathic α helix identified in this study may be conserved among this group of adenoviruses. In the alignment seen in FIG. 8, conserved arginine residues are shaded black. Basic amino acids found at the same position are shaded gray and divergent amino acids are not shaded. With the exception of the canine Ad3 protein, each of these E4orf6 homologues contain a positively charged amino acid at the position equivalent to $R_{241}$ and $R_{243}$. All of these proteins preserve a net positive charge on the residues (240, 244, 248, and 251) that comprise the central face of the α helix. Thus, the key features of the arginine faced amphipathic α helix required for E1B-55 kDa protein nuclear localization are conserved among these viruses.

EXAMPLE 7

E4orf6 Variants are Not Cytotoxic to 293 Cells

Prolonged expression of the E4orf6 protein has adverse effects on the cell. By promoting exon skipping, the E4orf6 protein changes splicing patterns in both infected and in transfected cells. The E4orf6 protein is an oncogene that can bind and inhibit both p53 and p73. Furthermore, the E4orf6 protein cooperates with the 12S E1A protein to induce cell transformation in baby rat kidney cells. Curiously, these transformed cells fail to express the E4orf6 protein. It has been proposed that these cells become transformed by acquiring mutations in cellular growth regulatory genes. In support of this notion, expression of the E4orf6 and E1A proteins in Chinese hamster ovary cells increases the mutation frequency at the chromosomal hypoxanthine phosphoribosyltransferase (HPRT) locus. These activities may contribute to the ostensibly cytotoxic nature of the E4orf6 protein. In turn, this cytotoxic nature of the E4orf6 protein may preclude the establishment of permanent cell lines that express the E4orf6 protein.

For adenovirus replication, the E4orf6 protein provides the essential function of the E4 region of adenovirus. Therefore, for the purposes of propagating recombinant, defective adenovirus vectors, it would be highly desirable to create cell lines that express the E4orf6 protein along with other key adenovirus growth regulatory gene products. These complementing cell lines would allow for the efficient replication of adenovirus vectors that lack the E4 region and other adenovirus genes.

Replication of adeno-associated virus (AAV) requires the Rep proteins of AAV, and the E1B-55 kDa, E4orf6 and E2A proteins of adenovirus as well as the small virus associated RNAs (VA RNA) of adenovirus. Cell lines that express all of these products except for the E4orf6 protein have been established. The ability to stably express the E4orf6 protein in these cell lines would allow for the efficient, large-scale production of recombinant AAV free of contaminating helper virus.

The work described in Examples 1–6 above reports E4orf6 protein variants that failed to exhibit a functional interaction with the E1B-55 kDa protein. However, some of these variants provided wild-type E4orf6 function in a virus complementation assay. This example further demonstrates that these key E4orf6 variants are not cytotoxic to 293 cells and therefore can be used for the creation of cell lines that express a functional E4orf6 product.

Figure 9:
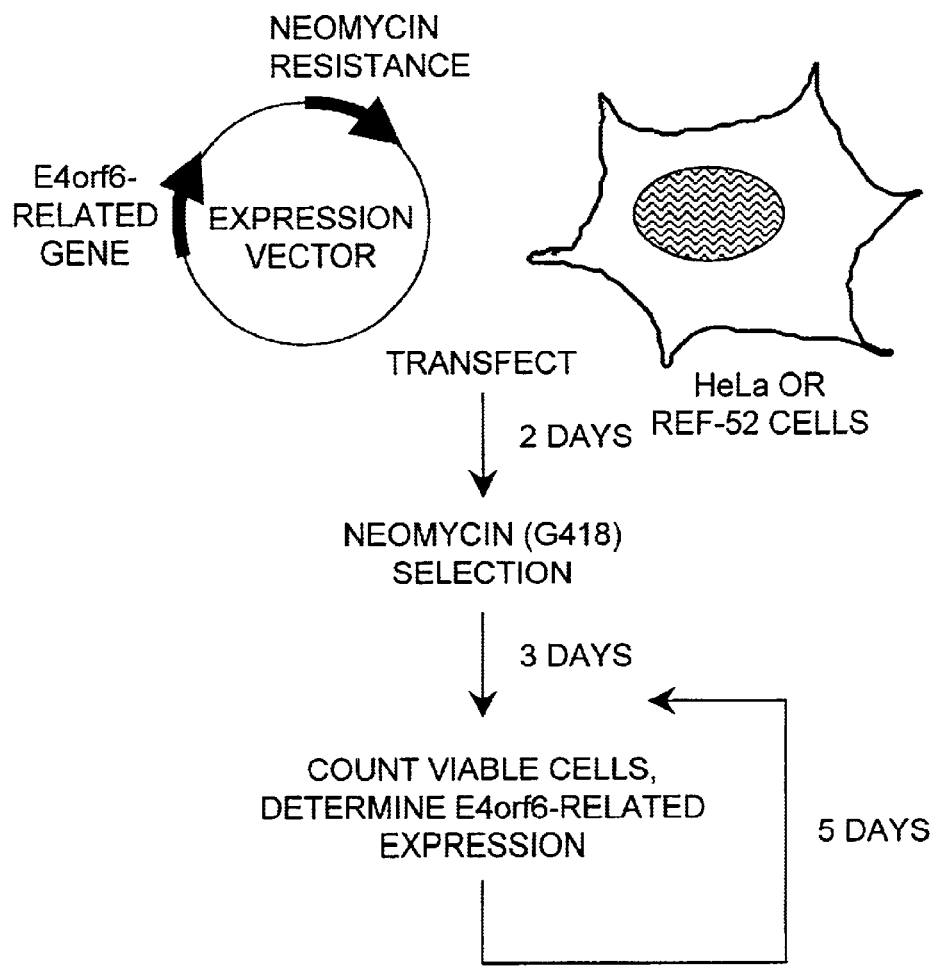
FIG. 9 shows the E4orf6 expression and cell survival experimental protocol. HeLa cells, derived from a human cervical carcinoma, or REF-52, a spontaneously immortalized cell line derived from rat embryo fibroblasts, were transfected with plasmids expressing both the neomycin resistance gene and an E4orf6-related cDNA. Two days after transfection, the cells were placed under antibiotic selection with 600 µg/ml G418. Every 5$^{th}$ day, a portion of cells were harvested and the selective medium was replenished. Viability was determine by Trypan Blue exclusion. The fraction of cells expressing the E4orf6-related proteins was determined by immunofluorescence.
Figure 10:
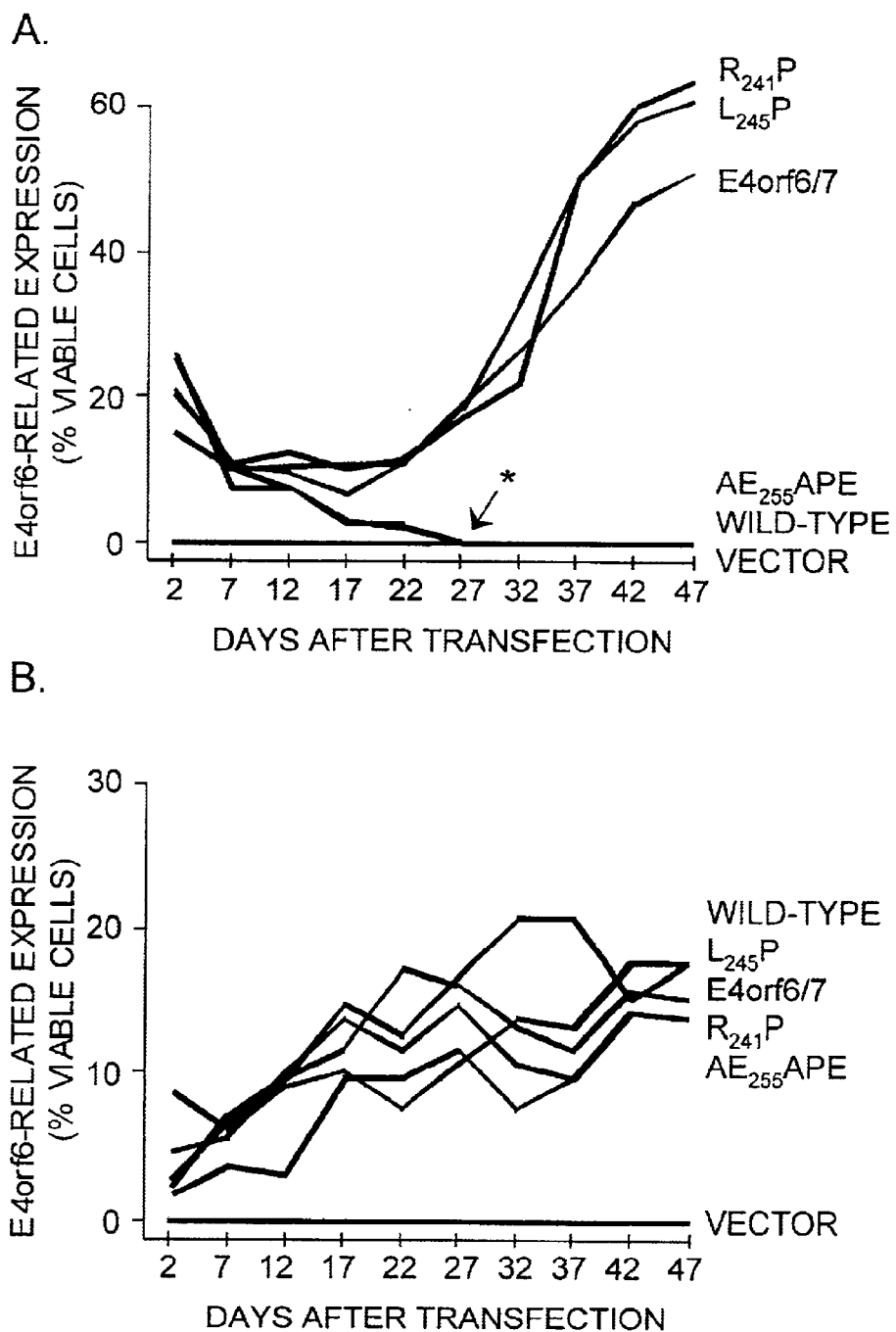
FIG. 10 (Parts A–B) shows the expression of the wild-type E4orf6 protein cannot be sustained and is deleterious to HeLa cells but not REF-52 cells. HeLa cells and REF-52 cells were transfected with the E4orf6-related constructs indicated on the right of each graph and placed under selection according to the protocol described in FIG. 9. The percent of cells expressing the E4orf6-related protein is shown as a function of time after transfection and selection. All non-transfected cells were killed within 14 days of selection. (A) HeLa cells tolerate stable expression of the non- functional E4orf6 variants ($R_{241}P$, $L_{245}P$, and E4orf6/7) but not the wild-type protein nor the functionally wild-type praline-variant, $AE_{255}APE$. After 27 days following transfection (indicated by the arrowhead), no cells remained in the samples transfected with the wild-type construct or the $AE_{255}APE$ construct. (B) REF-52 cells tolerate stable expression of all E4orf6-related constructs.

Expression of the wild-type E4orf6 protein cannot be sustained in HeLa or 293 cells. The vector pCMV-Neo-Bam was used to force simultaneous expression of both the neomycin phosphotransferase gene and the E4orf6 protein or related variants (FIG. 9). Selection for expression of the associated E4orf6 gene can be achieved by subjecting the cells to selection by the antibiotic G418. Under these circumstances, only cells expressing the neomycin resistance gene can survive. Initially, all of these cells also expressed the associated E4orf6 protein. An analysis of the time course of cell survival and E4orf6 expression shows that expression of the E4orf6 protein or the functionally wild-type $AE_{255}APE$ variant (Orlando and Ornelles, 1999) cannot be sustained in HeLa cells (FIG. 10) or 293 cells (data not shown).

In the experiment reported in FIG. 10A, approximately 20% of the transfected HeLa cells initially expressed the E4orf6-related protein. Under continued antibiotic selection, survival of the transiently transfected cells requires quasistable integration of the plasmid into the chromosomal DNA. After approximately two weeks of selection, the fraction of cells expressing the non-functional E4orf6-related proteins began to increase, presumably reflecting the outgrowth of stable integrants. By contrast, expression of the wild-type E4orf6 protein and of a variant that preserved wild-type function could not be sustained. Moreover, under antibiotic selection, all of these cells failed to survive beyond four weeks. This effect was not observed in the non-permissive cell lined derived from rat embryo fibroblasts, REF-52. In this cell line, stable expression of all of the E4orf6-variants was observed through the course of the experiment (FIG. 10B). The significance of this cell type specific difference remains unclear although it may reflect the consequences of the interaction between the E4orf6 protein and specific cellular factors.

E4orf6 cytoxicity varies among human cell lines. The cytotoxic nature of the E4orf6 protein is evident by the inability to form antibiotic-resistant colonies of cells when expression of both the neomycin-resistance gene and the E4orf6 gene are linked. This assay was applied to the cells indicated in FIG. 11. As in FIG. 10, REF-52 cells tolerated expression of the wild-type E4orf6 protein and the number of neomycin-resistant cell colonies recovered after transfection of the vector alone or the functionally defective $L_{245}P$ variant was equivalent to the number of neomycin-resistant colonies that also expressed the wild-type E4orf6 protein (FIG. 11A). In contrast to the REF-52 cells but similar to the results obtained with HeLa cells, 293 cells would not tolerate forced expression of the wild-type E4orf6 protein (FIG. 11B). However, consistent with reports of other investigators, two additional human cell lines, the osteosarcoma-derived SAOS-2 cells and the lung carcinoma-derived A549 cells, would tolerate forced expression of the wild-type E4orf6 protein. The significance of these cell-type specific differences remains unclear although it does further support that notion that the toxic nature of the E4orf6 protein derives from an interaction of the viral protein and cell type-specific factors.

Select E4orf6 variants that support the growth of adenovirus are not cytotoxic to 293 cells. The E4orf6 variants initially described were tested for cytoxicity in 293 cells as described in the legend to FIG. 11. As expected, variants that were devoid of E4orf6 activity during a viral infection (shown by light bars) were not toxic to 293 cells. However, expression of three variants that also provided wild-type E4orf6 function, $R_{241}E$, $R_{243}E$, and $R_{240,51}E$, could be sustained in 293 cells and numerous stable, neomycin-resistance cell colonies could be recovered from 293 cells transfected with these constructs. A fourth variant, $R_{240,44,51}A$ which also provided wild-type E4orf6 function during adenovirus growth was found to be less cytotoxic than the wild-type E4orf6 protein but more cytotoxic than the arginine to glutamic acid substitution variants. It should be noted that in previous experiments, the rare antibiotic-resistance colonies that arose after transfection of the wild-type E4orf6 construct typically could not be subcloned. Moreover, the few colonies that could be propagated further, failed to express detectable E4orf6 protein and contained undetectable levels of E4orf6 cDNA (less than one E4orf6 gene per cell).

The glutamic acid substitution E4orf6 variants, $R_{241}E$, $R_{243}E$, and $R_{240,51}E$, provide wild-type E4orf6 function during an adenovirus infection. It seems likely that these variants also provide the E4orf6 function required for AAV replication. Nonetheless, these E4orf6 protein variants are not cytotoxic to 293 cells. Therefore, the cDNA encoding these variants can be used to create stable cell lines that express E1A, E1B and, for the first time, E4 function.

The foregoing examples are illustrative of the present invention, and are not to be construed as limiting thereof. The invention is described by the following claims, with equivalents of the claims to be included therein.

What is claimed is:

1. A method of packaging a recombinant viral vector, comprising the steps of:
   (a) providing a packaging cell, said packaging cell containing and expressing a nucleic acid encoding a mutant adenovirus E4orf6 protein, said E4orf6 protein containing at least one mutation in the region encoding amino acids 230 to 260 wherein said at least one mutation comprises a substitution mutation at position 240, 241, 243, 244, 248, or 251;
   (b) transfecting or infecting said packaging cell with a nucleic acid that encodes a recombinant viral vector selected from the group consisting of adenovirus vectors and adeno-associated virus vectors, wherein said vector lacks a functional gene encoding E4orf6 protein; and wherein said mutation renders said mutant adenovirus E4orf6 protein non-toxic to said transfected cells;
   (c) culturing said transfected cells under conditions that permit expression of the mutant E4orf6 protein and the production of packaged recombinant viral vector therein: and then
   (d) collecting packaged recombinant viral vector from said cultured cells.

2. The method according to claim 1, wherein said mutation disrupts the interaction of the E4orf6 protein and the E1B-55kDa protein in said host cell.

3. The method according to claim 1, wherein said packaging cell is transiently transfected with said nucleic acid encoding said mutant adenovirus E4orf6 protein.

4. The method according to claim 1, wherein said packaging cell is stably transfected with said nucleic acid encoding said mutant adenovirus E4orf6 protein.

5. The method according to claim 1, wherein said nucleic acid encoding said mutant adenovirus E4orf6 gene is carried by a plasmid, bacteriophage, cosmid or retrovirus.

6. The method according to claim 1, in which said at least one substitution mutation is a substitution of arginine for an amino acid selected from the group consisting of glutamic acid, aspartic acid, serine, threonine, alanine and glutamine.

7. The method according to claim 1, wherein said nucleic acid encoding said mutant adenovirus E4orf6 protein encodes (i) an arginine 241 to glutamic acid substitution mutation, (ii) an arginine 243 to glutamic acid substitution mutation, or (iii) both an arginine 241 to glutamic acid substitution mutation and an arginine 243 to glutamic acid substitution mutation.

8. The method according to claim 1, wherein said nucleic acid encoding said mutant adenovirus E4orf6 protein encodes (i) an arginine 240 to glutamic acid substitution mutation, (ii) an arginine 251 to glutamic acid substitution mutation, or (iii) both an arginine 240 to glutamic acid substitution mutation and an arginine 251 to glutaniic acid substitution mutation.

9. The method according to claim 1, wherein said viral vector is an adenovirus vector.

10. The method according to claim 1, wherein said viral vector is an adeno-associated virus vector.

11. A packaging cell, said packaging cell containing and expressing a nucleic acid encoding a mutant adenovirus E4orf6 protein, said E4orf protein containing at least one mutation in the region encoding amino acids 230 to 260 wherein said at least one mutation comprises a substitution mutation at position 240, 241, 243, 244, 248, or 251 that renders said protein non-toxic to a host cell in which said protein is expressed.

12. The packaging cell according to claim 11, wherein said at least one mutation disrupts the interaction of the E4orf6 protein with the E1B-55kDa protein in a host cell.

13. The packaging cell according to claim 11, wherein said packaging cell is stably transfected with said nucleic acid encoding said mutant adenovirus E4orf6 protein.

14. The packaging cell according to claim 11, wherein said nucleic acid encoding said mutant adenovirus E4orf6 protein is carried by a plasmid, bacteriophage, cosmid or retrovirus.

15. The packaging cell according to claim 11, in which said at least one substitution mutation is a substitution of arginine for an amino acid selected from the group consisting of glutamic acid, aspartic acid, serine, threonine, alanine and glutamine.

16. The packaging cell according to claim 11, wherein said nucleic acid encoding said mutant adenovirus E4orf6 gene encodes (i) an arginine 241 to glutamic acid substitution mutation, (ii) an arginine 243 to glutamic acid substitution mutation, or (iii) both an arginine 241 to glutamic acid substitution mutation and an arginine 243 to glutamic acid substitution mutation.

17. The packaging cell according to claim 11, wherein said nucleic acid encoding said mutant adenovirus E4orf6 gene encodes (i) an arginine 240 to glutamic acid substitution mutation, (ii) an arginine 251 to glutamic acid substitution mutation, or (iii) both an arginine 240 to glutamic acid substitution mutation and an arginine 251 to glutamic acid substitution mutation.

18. A nucleic acid encoding a mutant adenovirus E4orf6 protein, said E4orf6 protein containing at least one mutation in the region encoding amino acids 230 to 260 wherein said at least one mutation comprises a substitution mutation at position 240, 241, 243, 244, 248, or 251 that renders said protein non-toxic to a host cell in which said protein is expressed.

19. The nucleic acid according to claim 18, in which said at least one mutation disrupts the interaction of the E4orf6 protein with the E1B-55kDa protein in a host cell.

20. The nucleic acid according to claim 18, wherein said nucleic acid is a DNA.

21. The nucleic acid according to claim 18, wherein said nucleic acid is a plasmid, bacteriophage, plasmid or retrovirus.

22. The nucleic acid according to claim 18, in which said sat least one substitution mutation is a substitution of arginine for an amino acid selected from the group consisting of glutaniic acid, aspartic acid, serine, threonine, alanine and glutamine.

23. The nucleic acid according to claim 18, wherein said nucleic acid encodes (i) an arginine 241 to glutamic acid substitution mutation, (ii) an arginine 243 to glutamic acid substitution mutation, or (iii) both an arginine 241 to glutamic acid substitution mutation and an arginine 243 to glutamic acid substitution mutation.

24. The nucleic acid according to claim 18, wherein said nucleic encodes (i) an arginine 240 to glutamic acid substitution mutation, (ii) an arginine 251 to glutamic acid substitution mutation, or (iii) both an arginine 240 to glutamic acid substitution mutation and an arginine 251 to glutamic acid substitution mutation.

* * * * *

UNITED STATES PATENT AND TRADEMARK OFFICE
CERTIFICATE OF CORRECTION

PATENT NO.    : 6,844,192 B2
DATED         : January 18, 2005
INVENTOR(S)   : Orlando et al.

It is certified that error appears in the above-identified patent and that said Letters Patent is hereby corrected as shown below:

Column 4,
Line 33, should read -- arginine to lysine substitutions within the amphiphatic α --
Line 36, should read -- athic α helix (E4orf6 residues 239-255, SEQ ID NO:26) and --
Line 39, should read -- ID NO:27). (B) HeLa cells were infected with a recombinant --
Line 41, should read -- polymerase and then transfected with cDNA under control --
Line 59, should read -- immunoblotting with MAb 3 (Marton et al. (1990) *J. Virol.* --

Column 5,
Line 63, should read -- tation of the α helical peptides is the same as seen in FIG. 1B --

Column 6,
Line 2, should read -- $R_{240,244,251}A$, 62%; (G) $R_{241}E$, 0.8%. --
Line 22, should read -- FIG. 8 shows the key features of the amphipathic α helix --
Line 31, should read -- region corresponding to amphipathic α helix. The arginine --

Column 7,
Line 1, should read -- cytotoxicity is cell type-specific. The cells indi- --
Line 8, should read -- presence of 600 µg/ml G418. After 21 days, the number of --

Column 38,
Line 52, should read -- substitution mutation and an arginine 251 to glutamic acid --

Column 40,
Line 15, should read -- ing of glutamic acid, aspartic acid, serine, threonine, alanine --

Signed and Sealed this

Twelfth Day of July, 2005

JON W. DUDAS
*Director of the United States Patent and Trademark Office*

SEQUENCE LISTING

<160> NUMBER OF SEQ ID NOS: 34

<210> SEQ ID NO 1
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 1
cgctgctgtg ccgaggagac aaggcgcct                              29

<210> SEQ ID NO 2
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 2
cgccttatgc tggaggcggt ggaaatcatc gctga                        35

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3
gcccggagga cagaggagct tatgctgcgg                              30

<210> SEQ ID NO 4
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 4
gcccggagga cagagcgcct tatgctg                                 27

<210> SEQ ID NO 5
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 5
cggaggacaa gggagcttat gctgcgg                                 27

<210> SEQ ID NO 6
<211> LENGTH: 30
<212> TYPE: DNA

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 6
gcaacggcag cgctcatgct agcagcggtg                              30

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
caccgctgct agcatgagcg ctgccgttgc                              30

<210> SEQ ID NO 8
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 8
aagaccaaga agcttatgct gaaggcagta                              30

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 9
tactgccttc agcataagct tcttggtctt                              30

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 10
ggtgcgctgc tgcgcagaga ggacaaggcg                              30

<210> SEQ ID NO 11
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 11
gctgctgtgc ccgggagaca aggcgcctta t                            31

<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 12
ggcgccttat gctcgaggcg gtgcgaatc                               29

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 13
gctgcgggcg gtcgaaatca tcgctgagg                                29

<210> SEQ ID NO 14
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 14
ggtgcgctgc tgtgcagctg cgacaaggcg ccttatg                       37

<210> SEQ ID NO 15
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 15
gcccggagga cagctgccct tatgctgcgg                               30

<210> SEQ ID NO 16
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 16
ggcgccttat gctggcagct gtggcaatca tcgctgagga g                  41

<210> SEQ ID NO 17
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 17
gcgctgctgt gccgcgcgca caaggcgcct tatg                          34

<210> SEQ ID NO 18
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 18
gctgcgggcg gtcgcgatta tcgctgagga gacc                          34

<210> SEQ ID NO 19
<211> LENGTH: 24
<212> TYPE: DNA
<213> ORGANISM: Artificial sequence
<220> FEATURE:

```
<223> OTHER INFORMATION: Synthetic oligonucleotide

<400> SEQUENCE: 19
cccggaggac agcgcgcctt atgc                                              24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
cgcgcacaag agctcttatg ctgc                                              24

<210> SEQ ID NO 21
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 21
ccttatgctg gcggccgtcg cgattatc                                          28

<210> SEQ ID NO 22
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 22
ctgctgtgcc cgggcgacaa ggcgccttat g                                      31

<210> SEQ ID NO 23
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 23
ccggaggaca agggccctta tgctgcgggc                                        30

<210> SEQ ID NO 24
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 24
ggcgccttat gctggcggcc gtgcgaatca tcg                                    33

<210> SEQ ID NO 25
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 25
gagctcttat gctagcggcg gtcgcgatt                                         29
```

```
<210> SEQ ID NO 26
<211> LENGTH: 17
<212> TYPE: PRT
<213> ORGANISM: Human adenovirus type 2

<400> SEQUENCE: 26

Ala Arg Arg Thr Arg Arg Leu Met Leu Arg Ala Val Arg Ile Ile Ala
1               5                  10                  15
Glu

<210> SEQ ID NO 27
<211> LENGTH: 17
<212> TYPE: PRT
<213> ORGANISM: Artificial sequence
<220> FEATURE:
<223> OTHER INFORMATION: R4K mutant Ad E4orf6 amino acids 239-255

<400> SEQUENCE: 27

Ala Arg Lys Thr Lys Lys Leu Met Leu Lys Ala Val Arg Ile Ile Ala
1               5                  10                  15
Glu

<210> SEQ ID NO 28
<211> LENGTH: 17
<212> TYPE: PRT
<213> ORGANISM: Human adenovirus type 9

<400> SEQUENCE: 28

Ala Arg Arg Thr Arg Arg Leu Met Leu Lys Ala Val Gly Ile Ile Ala
1               5                  10                  15
Arg

<210> SEQ ID NO 29
<211> LENGTH: 17
<212> TYPE: PRT
<213> ORGANISM: Human adenovirus type 17

<400> SEQUENCE: 29

Ala Arg Arg Thr Arg Arg Leu Met Leu Arg Ala Val Gly Ile Ile Ala
1               5                  10                  15
Arg

<210> SEQ ID NO 30
<211> LENGTH: 17
<212> TYPE: PRT
<213> ORGANISM: Human adenovirus type 12

<400> SEQUENCE: 30

Ala Arg Arg Thr Arg Leu Leu Met Leu Lys Val Val Gln Val Ile Ala
1               5                  10                  15
Glu

<210> SEQ ID NO 31
<211> LENGTH: 17
<212> TYPE: PRT
<213> ORGANISM: Human adenovirus type 40

<400> SEQUENCE: 31

Ala Arg Arg Thr Arg Arg Leu Leu Ala Lys Ala Val Lys Val Leu Gly
1               5                  10                  15
Ser
```

```
<210> SEQ ID NO 32
<211> LENGTH: 17
<212> TYPE: PRT
<213> ORGANISM: Porcine adenovirus 3

<400> SEQUENCE: 32

Ala Gln Arg Leu Arg His Trp Leu Lys Leu Ala Ala Glu Ala Ile Gly
1               5                   10                  15

Ala

<210> SEQ ID NO 33
<211> LENGTH: 17
<212> TYPE: PRT
<213> ORGANISM: Bovine adenovirus type 3

<400> SEQUENCE: 33

Leu Lys Arg Cys Lys Gln Lys Ile Arg Tyr Met Leu Asn Leu Ala Pro
1               5                   10                  15

Lys

<210> SEQ ID NO 34
<211> LENGTH: 16
<212> TYPE: PRT
<213> ORGANISM: Canine adenovirus type 1

<400> SEQUENCE: 34

Ala Phe Trp Val Arg Ser Ile Ile Asp Arg Val Leu Arg Glu Val Glu
1               5                   10                  15
```